US011026635B2

(12) United States Patent
Zingaretti et al.

(10) Patent No.: US 11,026,635 B2
(45) Date of Patent: Jun. 8, 2021

(54) SYSTEMS AND METHODS FOR HAIR LOSS MANAGEMENT

(71) Applicant: Restoration Robotics, Inc., San Jose, CA (US)

(72) Inventors: Gabriele Zingaretti, Capitola, CA (US); Miguel G. Canales, Los Altos, CA (US); James W. McCollum, Coronado, CA (US)

(73) Assignee: Restoration Robotics, Inc., San Jose, CA (US)

(*) Notice: Subject to any disclaimer, the term of this patent is extended or adjusted under 35 U.S.C. 154(b) by 229 days.

(21) Appl. No.: 15/996,256

(22) Filed: Jun. 1, 2018

(65) Prior Publication Data

US 2018/0271456 A1 Sep. 27, 2018

Related U.S. Application Data

(62) Division of application No. 14/814,458, filed on Jul. 30, 2015, now Pat. No. 10,013,642.

(51) Int. Cl.
*G06K 9/46* (2006.01)
*A61B 5/00* (2006.01)
(Continued)

(52) U.S. Cl.
CPC .......... *A61B 5/7275* (2013.01); *A61B 5/0077* (2013.01); *A61B 5/1032* (2013.01);
(Continued)

(58) Field of Classification Search
CPC ..... A61B 34/30; A61B 5/0077; A61B 5/1032; A61B 5/446; A61B 5/448; A61B 5/486; A61B 5/7264; A61B 5/7275; A61B 5/7435; A61B 5/748; G06F 19/00; G06K 2009/4666; G06K 9/00268; G06K 9/46;
(Continued)

(56) References Cited

U.S. PATENT DOCUMENTS 6,571,003 B1 5/2003 Hillebrand et al.
6,585,746 B2 7/2003 Gildenberg
(Continued)

FOREIGN PATENT DOCUMENTS

WO 1998021695 5/1998
WO 2007041014 4/2007
(Continued)

OTHER PUBLICATIONS

International Search Report and Written Opinion of the International Searching Authority, dated Oct. 20, 2016, in connection with commonly assigned International (PCT) Application No. PCT/US2016/043292 (18 pages).

(Continued)

*Primary Examiner* — Nirav G Patel

(57) ABSTRACT

Comprehensive systems and methods for managing hair loss are provided which enable an individual experiencing hair loss, and/or the person consulting him or her, to manage it and to determine and efficiently plan any appropriate treatment options. Management of hair loss may comprise quantifying hair loss, determining what hair growth stimulation product or treatment to adopt and the best timing for such products and/or treatments, and allowing to track and manage any progress of the selected hair growth stimulation product or treatment.

6 Claims, 5 Drawing Sheets

110 Identify Predefined Region
120 Identify Site Locations
130 Determine Value Associated with Site
140 Assign Representation to Determined Value
150 Populate Predetermined Region with Representations at Site Locations
160 Determine Proportions of Each Type of Representation
170 Calculate Metric
100

(51) Int. Cl.

| | |
|---|---|
| ***G06T 7/00*** | (2017.01) |
| ***A61B 34/30*** | (2016.01) |
| ***A61B 5/103*** | (2006.01) |
| ***G06K 9/00*** | (2006.01) |
| ***G16H 20/40*** | (2018.01) |
| ***G16H 20/10*** | (2018.01) |
| ***G16H 50/20*** | (2018.01) |
| ***G16H 50/30*** | (2018.01) |
| ***G06K 9/62*** | (2006.01) |
| ***G06F 19/00*** | (2018.01) |

(52) U.S. Cl.

CPC .............. *A61B 5/446* (2013.01); *A61B 5/448* (2013.01); *A61B 5/486* (2013.01); *A61B 5/7264* (2013.01); *A61B 5/748* (2013.01); *A61B 5/7435* (2013.01); *A61B 34/30* (2016.02); *G06F 19/00* (2013.01); *G06K 9/00268* (2013.01); *G06K 9/46* (2013.01); *G06K 9/6267* (2013.01); *G06T 7/0012* (2013.01); *G16H 20/10* (2018.01); *G16H 20/40* (2018.01); *G16H 50/20* (2018.01); *G16H 50/30* (2018.01); *G06K 2009/4666* (2013.01); *G06T 2207/30088* (2013.01)

(58) Field of Classification Search

CPC ........ G06K 9/6267; G06T 2207/30088; G06T 7/0012; G16H 20/10; G16H 20/40; G16H 50/20; G16H 50/30

See application file for complete search history.

(56) References Cited

U.S. PATENT DOCUMENTS

| | | | |
|---|---|---|---|
| 6,985,611 | B2 | 1/2006 | Loussouarn et al. |
| 6,993,168 | B2 | 1/2006 | Loussouarn et al. |
| 7,083,611 | B2 | 8/2006 | Lemchen |
| 7,206,627 | B2 | 4/2007 | Abovitz et al. |
| 7,477,782 | B2 | 1/2009 | Qureshi et al. |
| 7,539,334 | B2 | 5/2009 | Corrion |
| 7,611,452 | B2 | 11/2009 | Allison et al. |
| 7,627,157 | B2 | 12/2009 | Qureshi et al. |
| 7,806,121 | B2 | 10/2010 | Bodduluri |
| 8,115,807 | B2 | 2/2012 | Rassman et al. |
| 8,199,983 | B2 | 6/2012 | Qureshi et al. |
| 8,945,150 | B2 | 2/2015 | Bodduluri et al. |
| 2004/0134084 | A1 | 7/2004 | Vanneste |
| 2005/0229418 | A1 | 10/2005 | Cohen |
| 2007/0012320 | A1 | 1/2007 | De Lacharriere et al. |
| 2007/0078466 | A1 | 4/2007 | Bodduluri et al. |
| 2009/0037280 | A1 | 2/2009 | Rabin et al. |
| 2012/0148127 | A1 | 6/2012 | Rassman et al. |
| 2013/0236074 | A1 | 9/2013 | Hillebrand et al. |
| 2014/0028822 | A1 | 1/2014 | Khadavi et al. |
| 2014/0261467 | A1 | 9/2014 | Zhang et al. |
| 2014/0278321 | A1 | 9/2014 | Zhang et al. |
| 2016/0193035 | A1 | 7/2016 | Silva Ramos et al. |
| 2016/0253799 | A1 | 9/2016 | Rahman et al. |

FOREIGN PATENT DOCUMENTS

| | | |
|---|---|---|
| WO | 2007041267 | 4/2007 |
| WO | 2012158379 | 11/2012 |
| WO | 2014150459 | 9/2014 |

OTHER PUBLICATIONS

Bernstein, et al., “Follicular Transplantation”, International Journal of Aesthetic and Restorative Surgery. vol. 3, No. 2., 1995, 119-132.

Bernstein, et al., “Standardizing the Classification and Description of Follicular Unit Transplantation and Micrografting Techniques”, American Society for Dermatologic Surgery Inc. 1998; 24, 957-963.

Bernstein, et al., “The Logic of Follicular Unit Transplantation”, Dermatologic Clinics vol. 17, No. 2,, Apr. 1999, 277-296.

Gibbons, et al., “Quantification of Scalp Hair—A Computer-Aided Methodology”, The Society for Investigative Dermatology, Inc. vol. 86. No. 1, Jan. 1986, 78-82.

Hoffman, “TrichoScan: A Novel Tool for the Analysis of Hair Growth In Vivo”, Journal of Investigative Dermatology, Nature Publishing Group, GB, vol. 8, No. 1,, Jun. 1, 2003, pp. 109-115.

Jimenez, et al., “Distribution of Human Hair in Follicluar Units—A Mathematical Model for Estimating the Donor Size in Follicular Unit Transplantation”, Dermatol Surg. 25:4, Apr. 1999, 294-298.

Neste, et al., “Critical Study of Hair Growth Analysis with Computer-Assisted Methods”, Journal European Academy of Dermatology and Venereology, 2006, 20, 578-583.

Paus, et al., “The Biology of Hair Follicles”, The New England Journal of Medicine. vol. 341, No. 7., 491-497.

Rassman, et al., “Micrografting in Extensive Quantities”, http://www.newhair.com/resources/mp-1995-micrografting.asp, (7 pages).

Wilhelmus, “Hair Transplantation Surgery”, Clinics in Dermatology. Oct.-Dec. 1987. vol. 5. No. 4. Chapter 7, 81-89.

210a
210b
220
200
230
230
220
250a
240
260a
270a
220
220

200
220
220
230
230
250b
240
260b
270b
220
220

SYSTEMS AND METHODS FOR HAIR LOSS MANAGEMENT

CROSS-REFERENCE TO RELATED APPLICATIONS

This application is a Divisional of U.S. application Ser. No. 14/814,458, filed Jul. 30, 2015.

FIELD OF THE APPLICATION

This application relates generally to management of cosmetic and dermatological procedures. In particular, this application relates to hair loss management systems, devices and methods of their use, including hair transplantation planning systems or other systems, devices and apparatus for planning hair loss treatment options and methods of their use.

BACKGROUND OF THE APPLICATION

Hair loss is a common problem experienced by many, both men and women, with the loss of hair being temporary or a gradual process leading to a permanent loss. There are numerous reasons for hair loss, including for example a deficiency/excess in vitamins, minerals, or other elements required for a healthy diet, hormonal changes, a trauma (such as that resulting from a surgical procedure, an accident, excessive weight loss, or a stressful event such as pregnancy), stress, a medical condition such as diabetes, male/female patterned baldness, or age. In other instances hair loss may result from the intake of certain medications, be a side-effect of certain drugs, or result from the excessive use of hair treatments.

The solution to the problem of hair loss, whether the hair loss is temporary, progressive or permanent, varies from patient to patient. An individual's decision on how to cope with their hair loss is based on a combination of factors, typically including whether the individual is male or female, their age, ethnicity, genetic disposition, health and diet considerations, personal goals or desires, and/or the stage of their hair loss. In addition, the availability and associated cost of options available, the inconvenience caused in terms of preparation time, procedure time, recovery time, pain and/or discomfort, peer tolerance or acceptance, input provided from friends, family and consultants, and emotion also play a role.

Depending upon the reason for hair loss, the solutions to remedy the temporary or permanent problem are as numerous as the reasons for hair loss. Solutions including, but not limited to, the use of products that can be applied topically to promote hair growth and/or reduce hair loss, special shampoos and other applications, wigs, laser treatments or surgical solutions such as hair transplantations.

Hair transplantation procedures are well-known, and typically involve (e.g., in a patient having male pattern baldness) harvesting donor hair grafts from the side and back fringe areas ("donor areas") of the patient's scalp, and implanting the harvested follicular units in a bald area ("recipient area"). Commonly assigned U.S. Pat. No. 6,585,746 discloses a hair transplantation system utilizing a robotic system, including a robotic arm and a hair follicle introducer associated with the robotic arm. An imaging system is used to produce a three-dimensional image of the patient's scalp, which is used to plan the locations to receive hair grafts. Hair transplantation procedures that are carried out using automated (including robotic) systems or computer-controlled systems have been described, for example, in U.S. Pat. No. 7,962,192, commonly owned by the assignee of the present application, which is incorporated herein by reference. After the robotic system has been initiated and calibrated, image data of the body surface is acquired and processed by the system computer to identify objects, in particular follicular units in a donor area, for example, on a human scalp. From images of this area of interest, image segmentation and screening software identifies and selects particular follicular units of interest for harvesting from the scalp.

Commonly assigned U.S. Pat. Nos. 7,806,121 and 8,104,480 (hereinafter collectively, "Bodduluri") illustrate systems and methods for planning transplantation of follicular units into a body surface of the patient. The entire disclosures of both above-identified U.S. patents are incorporated by reference.

SUMMARY

A variety of systems and methods for planning various cosmetic and dermatological procedures, including hair transplantation, are provided in the present application. These procedures may be performed on the scalp, face and other skin and body surfaces.

According to one aspect of the present application, a method for determining and managing hair loss on a body surface is provided. In various embodiments, the method comprises calculating a metric of hair loss or hair health. For example, the method may comprise: identifying one or more site locations on the body surface within a predetermined region; determining a value associated with each of the one or more site locations (each value may be determined, for example, by how many hair follicles (or in some embodiments hair grafts) are located within a boundary or certain area relative to the site location); assigning a representation to one or more of the determined values; populating the predetermined region with one or more representations of the determined values; determining proportions of each type of representation in the predefined region; and calculating a metric of hair loss or hair health based at least in part on the determined proportions.

In some embodiments, it may be determined if the hair or hair graft comprises one or more terminal hair based on, for example, one or more of a caliber, color, length or specifics of a particular patient. The size of the site location may vary depending on a particular implementation, in some embodiments it may be, for example, between 1-2 $cm^2$, and preferably 1 $cm^2$. A user may select an association between the determined values and the assigned representation via a remote input device, stylus, pen, finger(s), by drop-down menus, or touch screen commands and gestures.

In other embodiments the determined value comprises a first value if substantially no hair is located within the boundary of the site location, and a second value if one or more hairs are located within the boundary of the site location. In other embodiments the determined value further comprises a third value if two or more hairs are located within the boundary of the site location.

In various embodiments a visual representation of the body surface is populated with representations of the determined values for each of the plurality of site locations, showing an extent of hair loss. In other embodiments the value associated with the procedure site location is determined at a first and a second instance in time, and metric further comprises determining a difference in an area covered by each of the one or more representations between the first and the second instance in time. In some embodiments the first instance of time is prior to a hair treatment process having been performed, and the second instance in time is after a hair treatment process has been performed. In other embodiments the hair treatment process comprises a hair transplantation procedure, or an application of a hair treatment product, administering one or more medications or a therapy. According to a further aspect of the current disclosure a system is provided for determining and managing hair loss or hair health on a body surface, including, for example, a system for calculating a metrics of hair loss. The system may comprise: at least one non-transitory storage medium storing instructions, and one or more modules for executing operations on image data, the one or more modules comprising instructions for: identifying one or more site locations on the body surface within a predefined region; determining a value associated with each of the one or more site locations, each value determined by how many hairs are located within a boundary of the site location; assigning a representation to one or more of the determined values; populating the predefined region with one or more representations of the determined values; determining proportions of each type of representation in the predefined region; and calculating a metric of hair loss or hair health based at least in part on the determined proportions.

In a yet further aspect of the current disclosure a computer-implemented method for determining and managing hair loss on a body surface is provided, the method comprising: identifying one or more regions of interest (for example, potential recipient area or potential donor area) on a body surface; automatically determining a proportion of terminal and/or non-terminal hair within the one or more regions of interest; automatically analyzing proportions of classes of follicular units within the one or more regions of interest; and predicting a rate of advancement of hair loss based, at least in part, on the proportion of terminal and/or non-terminal hair and proportions of classes of follicular units within one or more regions of interest. In some implementations, the one or more regions of interest may be a potential donor area such that the methodology would allow to predict how much hair may be available in the future in such donor area based at least in part on the rate of advancement of the hair loss. In other implementations the method may comprise ranking of the one or more regions of interest based on the proportion of classes of follicular units.

In some embodiments, the method may further comprise assigning a hair loss value to the body surface and reassigning the hair loss value as of a future date based on the predicted rate of advancement of hair loss. In other embodiments, the method may comprise determining a number of follicular units in each class taking into consideration existence of terminal and non-terminal hair, wherein each class is based on a number of hair follicles in a follicular unit.

According to a still further aspect of the current disclosure, a system is provided for determining and managing hair loss on a body surface, the system comprising: at least one non-transitory storage medium storing instructions, and one or more modules for executing operations on image data, the one or more modules comprising instructions for: identifying one or more regions of interest on a body surface; automatically determining a proportion of terminal and/or non-terminal hair within the one or more regions of interest; automatically analyzing proportions of classes of follicular units within the one or more regions of interest; and predicting a rate of advancement of hair loss based, at least in part, on the proportion of terminal and/or non-terminal hair and proportions of classes of follicular units within the one or more regions of interest.

According to an additional aspect of the invention a computer implemented method is provided for determining and managing hair loss on a body surface, the method comprising: identifying regions on a body surface, the regions comprising a potential donor area and a potential recipient area; automatically determining proportion of terminal and/or non-terminal hair within the potential donor area and the potential recipient area; automatically analyzing proportions of classes of follicular units within the potential donor area; automatically analyzing proportions of classes of follicular units within the potential recipient area; and proposing one or more actions for managing hair loss based, at least in part, on the determined proportion of terminal and/or non-terminal hair, the proportions of classes of follicular units within the potential recipient area, and the proportions of classes of follicular units within the potential donor area. In some implementations, the method may comprise determining or proposing potential timing for performing a procedure or a treatment for hair loss. In some embodiments, the step of proposing one or more actions may be performed automatically by the automated system, in other embodiments a physician may choose one of several available options, for example, from a user interface, or use the results of the automated determination to propose an action or treatment option(s).

In some embodiments, the method may further comprise assigning a hair loss value to the body surface based on the identified regions. In other embodiments automatically analyzing proportions of classes of follicular units may further comprise determining a density in the potential donor area and automatically proposing that a hair transplantation procedure not be considered at present if the hair density is less than 40 hairs per 1 $cm^2$. In further embodiments, the method may comprise determining a density in the potential recipient area and automatically proposing that a hair transplantation be considered at present or during certain proposed time frame if the hair density is less than a predetermined number of hair follicles or follicular units per unit area. In certain embodiments the method may comprise determining a number of follicular units in each class taking into consideration existence of terminal and non-terminal hair follicles, wherein each class is based on a number of hair follicles in a follicular unit.

In a still further aspect of the current disclosure, a system for determining and managing hair loss on a body surface is provided, the system comprising: at least one non-transitory storage medium storing instructions, and one or more modules for executing operations on image data, the one or more modules comprising instructions for: identifying regions on a body surface, the regions comprising a potential donor area and a potential recipient area; automatically determining proportion of terminal and/or non-terminal hair follicles within the potential donor area and the potential recipient area; automatically analyzing proportions of classes of follicular units within the potential donor area; automatically analyzing proportions of classes of follicular units within the potential recipient area; and proposing one or more actions for managing hair loss based, at least in part, on the determined proportion of terminal and/or non-terminal hair follicles, the proportions of classes of follicular units within the potential recipient area, and the proportions of classes of follicular units within the potential donor area.

According to yet further aspects of the present disclosure, devices, systems and methods are provided that allow making treatment option decisions based on simulation and analysis of the development of the hair growth or hair loss of a subject over a period of time.

A method for using analysis of hair growth phase to plan hair transplantation is also provided. The method comprising: identifying one or more hair follicles within a predefined region on the body surface; determining a type of hair growth phase for the one or more hair follicles; determining a proportion of hair in an anagen hair growth phase; assigning a representation to and populating the predefined region with only those representations corresponding to hair in the anagen hair growth phase; and planning a hair transplantation procedure based, at least in part, on the determined proportion of the anagen hair and/or on a distribution of the populated representation.

According to yet another aspect, a method of determining which hairs to harvest from a donor area is provided. The method comprising: detecting hairs in an image of a donor area; determining which of the detected hairs are in an anagen growth phase; and determining which hairs to harvest from the donor area based on the determination of hairs in the anagen growth phase. In some embodiments the method further comprises harvesting fewer than all of the hairs identified as being in the anagen growth phase, such that some anagen growth phase hair remains in the donor area. In certain embodiments the method may further comprise automatically harvesting some or all of the determined hair, for example, by means of a robotic arm coupled to a hair harvesting tool.

In addition, a method for determining when to harvest hair from a body surface is provided, the method comprising: automatically comparing a first length of a hair at a first moment in time to a second length of the hair at a second moment in time and repeating the comparison for a plurality of hairs in a region of interest; automatically classifying compared hairs according to a hair growth phase based on a result of the comparison of the second length to the first length; automatically determining a proportion or percentage of hairs in the region of interest that are in an anagen hair growth phase; and determining when to plan a hair transplantation procedure based, at least in part, on the determined proportion or percentage of hairs.

Apparatus, devices and systems configured to implement any of the above methodologies are also provided.

Other and further objects and advantages of the invention will become apparent from the following detailed description when read in view of the accompanying figures.

BRIEF DESCRIPTION OF THE DRAWINGS

Features and advantages of the embodiments described herein will become appreciated as the same become better understood with reference to the specification, claims, and appended drawings wherein:

DETAILED DESCRIPTION OF THE PREFERRED EMBODIMENTS

Figure 1:
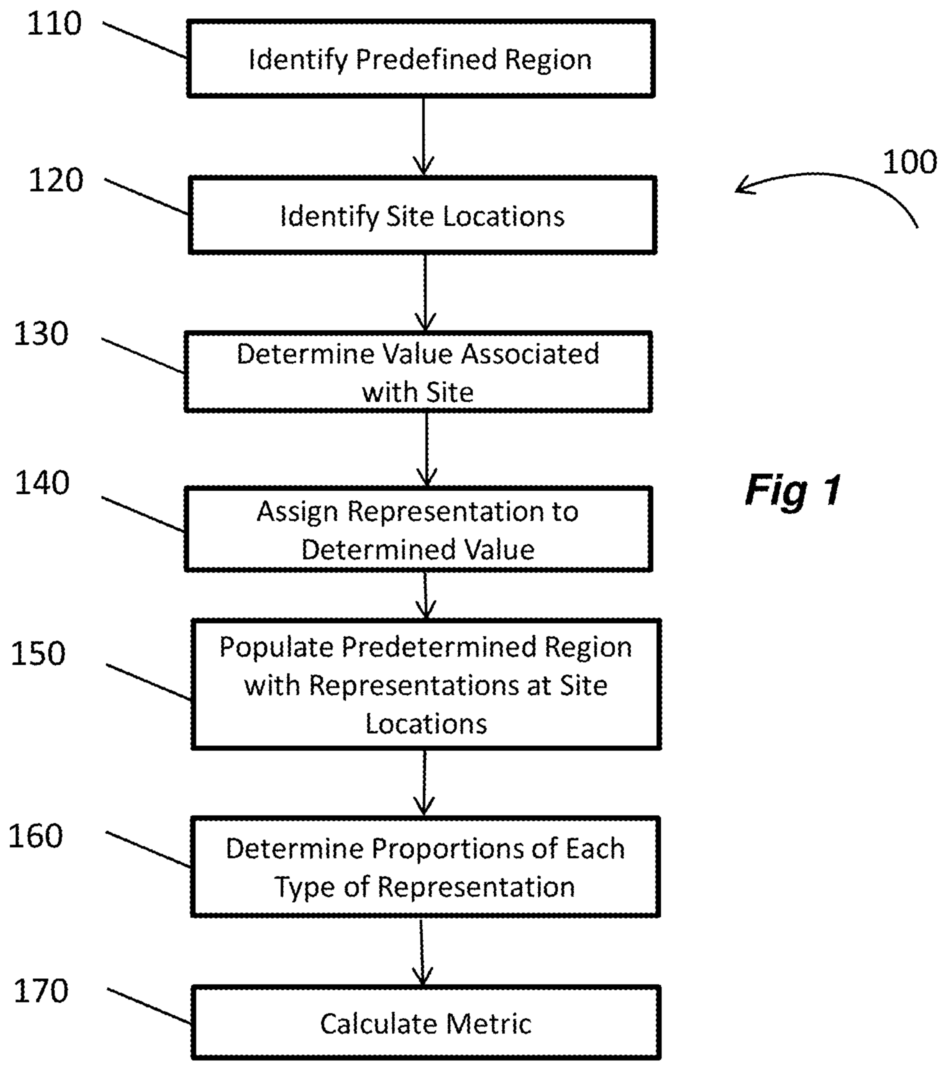
FIG. 1 is a flow chart illustrating an example of a general method for calculating a metric of hair loss.

With reference to the above-listed drawings, this section describes particular embodiments and their detailed construction and operation. The embodiments described herein are set forth by way of illustration only and not limitation. Those skilled in the art will recognize in light of the teachings herein that, for example, other embodiments are possible, variations can be made to the example embodiments described herein, and there may be equivalents to the components, parts, or steps that make up the described embodiments.

For the sake of clarity and conciseness, certain aspects of components or steps of certain embodiments are presented without undue detail where such detail would be apparent to skilled persons in light of the teachings herein and/or where such detail would obfuscate an understanding of more pertinent aspects of the embodiments.

Currently there are no comprehensive tools available to enable individuals to quantify their stage of baldness, make an informed personal choice, to assess whether they are making the most suitable decision (that is the best decision according to scientific evidence based on the individual's physical and mental status) or if the timing of their solution is being made at the stage of their hair loss process which would result in an optimum result. In addition, from the physician's perspective, there are no comprehensive tools available to assist managing and planning hair loss treatments, as well as the expectations that patients may have based on their individual hair loss.

Typically, an individual is first aware that he/she has a hair loss problem when they notice more scalp is visible, as their hair line recedes, they find more hair dropping out on a daily basis and eventually a bald spot appears. For most, there is a period of denial, or the belief that what they are experiencing is a short term issue, or temporary hair loss, and the hope that the loss will stop. By the time that they visit a professional, the progression of hair loss may be such that the opportunity to reduce the rate at which they lose hair is lost, more drastic measures are required to regain the appearance they seek, and/or the opportunity to transplant hair from areas with an ample hair supply has passed due to the overall reduction in hair density, leaving them with limited options, such as for example, wearing a wig. For others, due to genetic disposition, hair loss is expected, but they often do not know when it will begin, or the rate at which it will occur.

The present application provides comprehensive systems and methods for managing hair loss, enabling the individual experiencing hair loss and/or the physician consulting the patient to manage the hair loss process over a period of time, based upon one or more characteristics or parameters of the individual's hair loss, the one or more characteristics or parameters typically varying over time. Management of hair loss may comprise creating a metric of hair loss, identifying hair health of a patient, for example, by quantifying the stage of hair loss, managing hair loss to prevent or decrease the rate at which hair is being lost, or to restore at least some of the hair that may have been lost in some area(s). Management may comprise, but is not limited to, the selection of a particular hair enhancement product or treatment, a particular hair growth supplement, stem cell therapy, shampoo, topical application, or light/photo therapy, administering medication, or recommending/performing hair transplantation procedure. It also includes making suggestions and decisions related to the timing of when to implement the preceding options, including having a hair transplantation procedure performed. In addition, the present disclosure allows the individual and his or her physician to track progress of the selected hair enhancement product or treatment, allowing for the application of product or treatment to be modified or reconsidered, if required, over the treatment period.

According to another aspect of the current disclosure a method is also provided by which a physician is able to manage the expectation of a patient as to what can be achieved based on the proportions of follicular units he/she has. The present disclosure provides teachings for proposing not only the best solution to a patient's hair loss, but in addition proposing the time at which such solutions should be adopted or performed. Additionally, providing a comprehensive set of tools to enable one to quantify the level of success achieved by utilizing any particular solution.

Metric for Hair Loss

As indicated above, hair loss, or balding, is a complex condition, requiring an understanding of how far one's hair loss has progressed in order to receive the most suitable treatment. A practitioner typically diagnoses the stage of baldness based on appearance, along with a series of questions about one's medical history, and the history of hair loss in one's family. When visiting a practitioner, ideally one selects a practitioner of sufficient experience and skill such that they are able to quantify the stage of hair loss according to an accepted scale of hair loss, such as the Norwood scale, by comparing one's scalp and hair loss pattern to that of various stages 1-7 of the Norwood scale, or other such scale associated with hair loss. However in most situations it is difficult for any practitioner to quantify a person's baldness, for example if hair is long or curly, in some instances it may appear that one has more/less hair than he or she actually does. Depending upon the practitioner, during the examination a densitometer may also be used to attain a general idea of the degree of hair loss. The densitometer provides a measure of hair density in a unit area, such as an area of 10 $mm^2$ and that area is typically considered representative of the hair density throughout one's scalp. However utilizing such a device over one's entire scalp would be an extremely time consuming experience, and when all the results were computed, it would be difficult for any patient to interpret the results, a set of numbers. Consequently, quantifying one's hair loss is not a routine task, and therefore limits options that may otherwise be available to individuals with, for example, a genetic disposition to balding, to determine at what point in time he/she should consider a hair loss remedy, and perhaps what remedy should be utilized.

According to an aspect of the present disclosure, a methodology and corresponding apparatus and systems are provided for determining and managing hair loss on a body surface. This aspect provides for a determination of a metric of baldness to be assigned to a patient. In some embodiments according to this aspect of the disclosure a visual representation of data may be presented to the patient, physician or other user/operator. Such visual representation (including, for example, a map) assists the operator in quantifying a level of hair loss with respect to a patient. Such visual representations may be also used to plan future hair treatments, for example identifying areas within which medical topical solutions may be applied, areas which may serve as potential donor areas in a hair transplant, and those which may benefit as potential recipient areas in a future hair transplantation procedure. In some embodiment, such visual representations may also be used to track the success or otherwise of such medical treatments or hair transplantation procedures. Further, various representations also may be used in simulating or predicting a possible outcome of a procedure, in monitoring a procedure in real time, or in reviewing the results of a procedure (for example, a hair implantation procedure) at a later time. Such representations also may be used to simulate, plan or create hair implantation sites, as further described in detail in concurrently filed and co-owned patent application entitled "Systems and Methods for Creating Hair Transplantation Procedure Sites", the disclosure of which is incorporated herein by reference.

To aid in the present discussion, reference is made to FIGS. 1, 2*a*, 2*b* and 3, which illustrate non-limiting examples of a methodology and techniques for hair loss quantification which may be implemented on a computer system or one or more machines capable of executing program modules.

FIG. 1 is a flow chart illustrating an example of a general methodology 100 employed by one aspect of the present disclosure. FIG. 1 represents a block diagram of methods, apparatus (systems) and computer program products according to embodiments of the present disclosure. It will be understood that each block of the flowchart illustrations and/or block diagrams, and combinations of blocks in the flowchart illustrations and/or block diagrams, can be implemented by computer program instructions. The proposed steps may be substantially automated, which means that at least most of the steps could be performed automatically, for example, by a processor or other computing device. It does not exclude, however, that the user may intervene and participate, for example, by giving an alternative command through a user interface, or override the automated command.

Figure 2A:
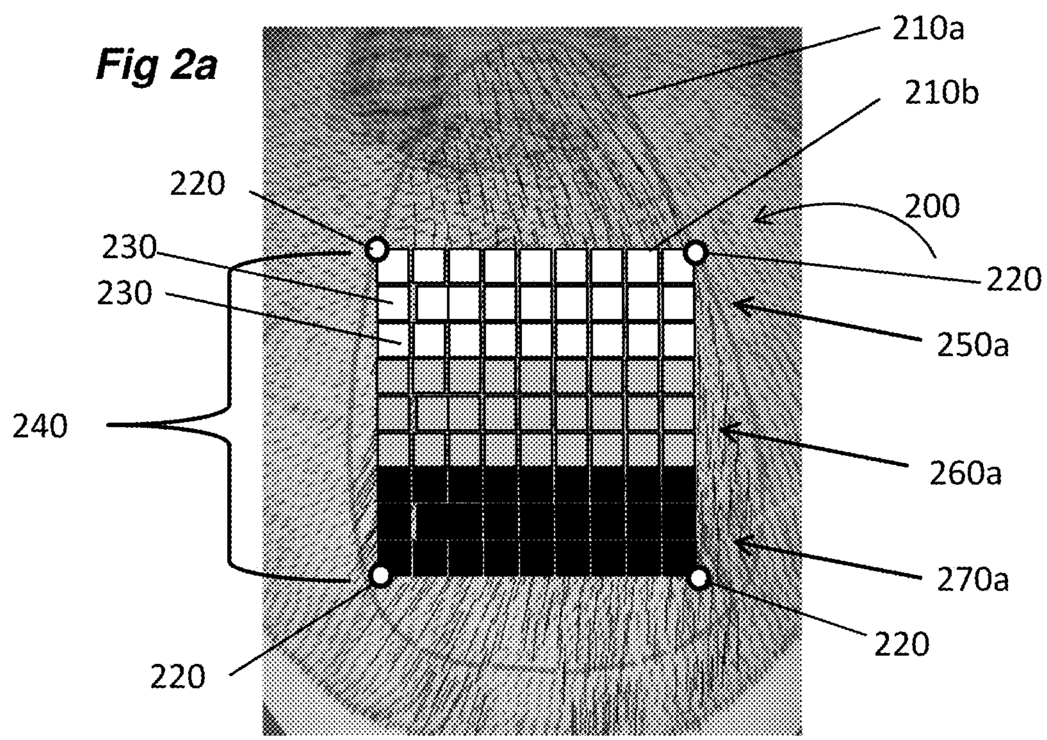
FIGS. 2*a* and 2*b* illustrate examples of the hair loss metric data representations, which may be created according to the methodology of FIG. 1.
Figure 2B:
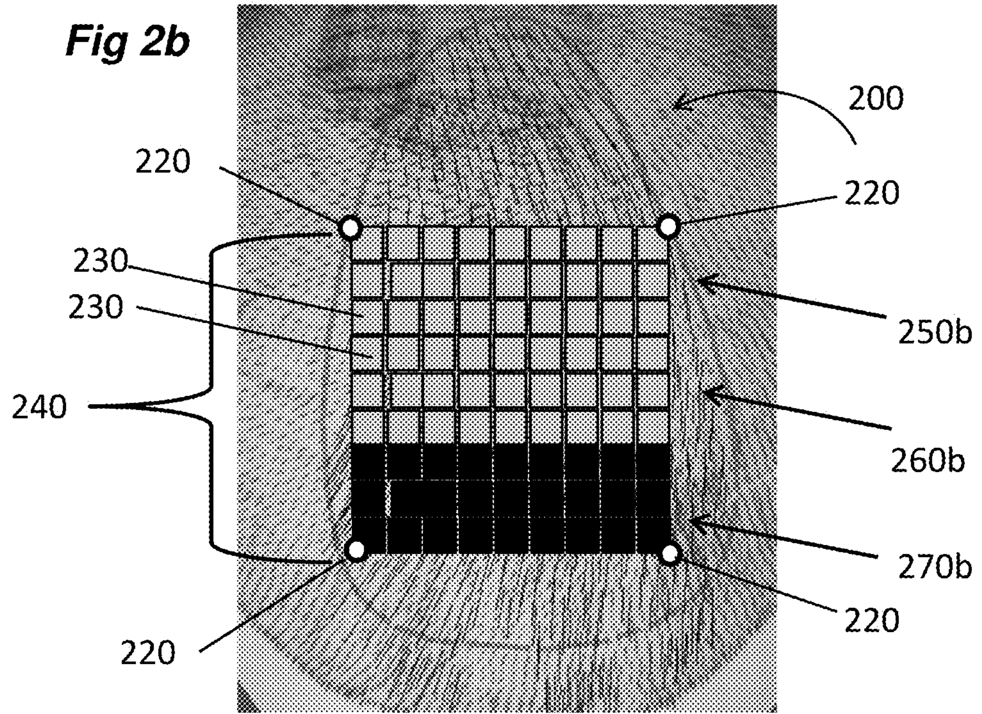

FIGS. 2*a* and 2*b* illustrate a representation of a body surface 200, with FIG. 2*a* representing the body surface 200 at a first instance in time $T_1$ (for example, a patient's first visit to the physician's office) and FIG. 2*b* representing the same body surface 200 at a second instance in time $T_2$ (for example, nine months after they have had a hair treatment applied, or a hair implantation procedure performed). In an alternative, $T_1$ may represent an image of a patient's scalp on his first visit to the physician's office, and $T_2$ may represent an image of the patient's scalp on a second or subsequent visit, when visiting his physician to determine the rate of hair loss, the progression of hair loss, assuming there is any, for example, 6-24 months later.

Prior to or as a part of the methodology of the present disclosure, the body surface 200, such as a scalp, for which the hair loss or baldness metric is required, is imaged. A predefined region 210, such as illustrated by either 210*a* or 210*b*, is subsequently identified (step 110). The predefined region 210(*a,b*) may comprise a large area of the scalp, including regions with hair, without and regions in-between. In one embodiment, the predefined region 210*a* may be identified or generated by the user, for example, by freehand drawing, using for example a mouse, stylus, pen or line tool on a touch-enabled device, tablet, or other such similar device, or by any other means known or later developed in the art, for example, directly on the scalp or an image of the scalp. In another embodiment, also illustrated in FIGS. 2*a* and 2*b*, the predefined region 210*b* may be identified using fiducials 220 (which may be disposed on the patient's body surface or a device place on the body surface) prior to imaging, providing reference points that are to be utilized to provide the boundaries of a predefined region 210 over which a baldness metric is to be determined. The fiducials 220 also may be, for example, physical markers or anatomical landmarks on a patient's skin or body surface, such as a follicular unit or hair, a mole, a scar, a freckle, a wrinkle, a bump, or a depression of the body surface. The fiducials 220 may also be objects placed on or affixed to the patient's skin, such a tattoo. A fiducial 220 is an object in a field of view of an imaging device that acts as a reference, and may comprise the above or any combination thereof. For the purposes of explanation, FIGS. 2*a* and 2*b* also illustrate by example a predefined region 210*b* illustrated as a square with each fiducials 220 positioned at each of the four corners of the predefined region 210*b*.

Referring to FIG. 2*a*, once the predefined region has been identified, one or more site locations 230 may be identified (step 120). The number of locations 230 utilized may be predetermined, selected automatically by the image processor, or selected by the user. In this particular example, a 9×9 array 240 provides a total of 81 site locations 230, each site location 230 comprising a square with dimensions, for example, of one centimeter squared (1 $cm^2$). To aid in the understanding of the disclosure, the 9×9 array 240 has been divided into three subsets, each subset comprising three rows of nine squares (3×9), 250*a*, 260*a* and 270*a*, the relevance of which will be discussed later. Initially, no color is assigned to any of the squares of the 9×9 array 240.

Figure 3:
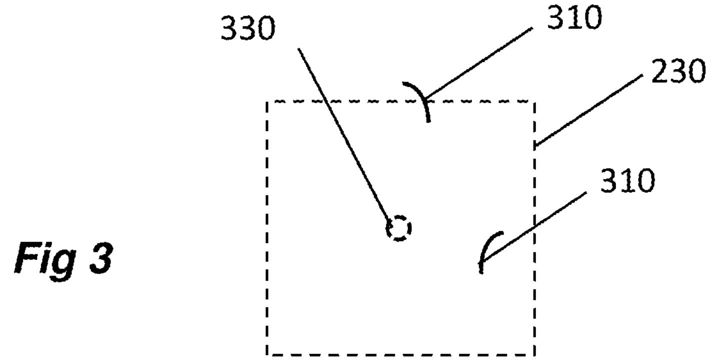
FIG. 3 is a schematic representation of an example of how the value associated with the site location may be determined.

The methodology illustrated in FIG. 1 enables visualization (via a user interface) of real time or near real time representations corresponding to values associated with unique or discrete site locations 230. For each identified site location 230, a determination is made of a value associated with the site location (step 130). In one embodiment of the disclosure, as illustrated in FIG. 3, the value may comprise the number of terminal hairs or hair follicles 310 within a boundary of the location site 230. The determination of which hairs are terminal hairs 120 may be carried out by various methodologies, and comprising one or more, or a combination, of the properties described below, determined for example by means of image processing. Non-terminal hair typically has a caliber of less than 35 μm or less than 0.05 mm, is lighter in color with respect to terminal hair on the same patient, and are generally shorter than terminal hair, for example, the average length of a vellus hair (one example of a non-terminal hair) ranging from 0.5-1.0 mm. To improve correct identification of the hair as terminal or non-terminal, a scoring system may be employed that gives certain weight to each of the above properties (e.g., caliber, color, lengths, etc.) and based on the weighted combined score the analyzed hair may be determined as terminal or non-terminal. It will be apparent however, that the caliber of terminal or non-terminal hair may vary from patient to patient. Therefore, according to another aspect of the disclosure, the user may take this into consideration and vary the value associated with a threshold considered for a particular patient to differentiate terminal and non-terminal hair. For example, if a patient has very light hair, then non-terminal hair may be almost translucent, or on a patient with very thick hair, a non-terminal hair may be thicker than the average thickness of other patients' non-terminal hair.

For example, depending on the application and qualities of hair of a particular individual, a terminal hair may be defined as having thickness of greater than sixty microns. Having determined the number of terminal hairs 310 within the boundary of the site location 230, a value associated with the site location 230 is thus determined (step 130), and subsequently a representation of that value can be assigned (step 140). Representations may be in a form of a color—for example, different colors representing different numbers of terminal hairs within the boundary of the site location. Alternatively, representations may comprise a shape (such as a circle, a square or a rectangle), the size of diameter of a dot, or any other such representation or combination of representations, which is capable of conveying a distinct meaning to the user. In various embodiments, a particular type of representation may be automatically provided by the automated system (e.g., a processor), or it may be defined or selected by the user, for example, via a user interface. According to some implementations, specific representations may be selected or customized by user interaction with a graphical user interface displayed on a visual display screen, by for example, utilizing drop down menus, selecting representation using text, allowing selection from a predetermined list, or by utilization of a drag and drop methodology. In one approach, a particular color is assigned to a discrete value or number of terminal hairs 310 that is determined to be within the boundaries of a site location 230.

It will be apparent that the numbers determining assignment of different representations may also vary. In the example illustrated, the color white is assigned to site locations which have fewer than 40 terminals hairs 310 within the 1 $cm^2$ site location 230. The color grey is assigned to site locations which have 40-70 terminal hairs 310 within the 1 $cm^2$ area of the site location 230, and the color black is assigned to site locations which have 70 or more terminal hairs 310 within a 1 $cm^2$ area of the site location 230. These values have been selected based on the typical number of hair, for a healthy head of hair, with respect to a patient who has had no hair enhancement treatments. For such a patient, assuming they are Caucasian, a typical number of hairs per 1 $cm^2$ area will range from 80-140 hairs. Therefore an area exhibiting hair loss of around 50% will have approximately 40-70 hairs in a 1 $cm^2$ area.

It will also be apparent that the colors and values described serve as examples only, and any color and value combination may be applied, depending upon the application in question and the desires of the user. In another example, a representation may comprise a first value if no terminal hairs are located within the site location, and a second value if one or more terminal hairs are located within the site location. In yet another example, rather than assigning a color to the entire area of the site location (the square of the array) as shown, a colored dot may be assigned to the center 330 of the site location, the colored dot indicating the number of terminal hairs 310 surrounding it. In an alternative, the actual number could appear, in a numerical format on the screen. The methodology continues for each site location 230, thereby dynamically displaying an indication of the terminal hairs 310 disposed at each site location 230.

FIG. 2*a* shows a representation of the body surface 200 populated (step 150 of the general methodology of FIG. 1) at site locations with the corresponding assigned representation superimposed thereon and displayed, for example, on a computer screen or such visual display for view by the operator.

As illustrated in FIG. 2*a*, the subset of 250*a*, the array of 9×3 comprises white squares, indicating in this particular example that the area covered by white squares is lacking terminal hairs, having fewer than 40 terminal hairs in each identified site location, and that the patient is effectively going bald in the region 250*a*. The subset of squares 260*a*, another array of 9×3 comprises grey squares, indicating in this particular example that the area covered by grey squares has 40-70 terminal hairs at each identified site location. The subset of squares 270*a*, another array of 9×3 comprises black squares, indicating in this particular example that the area covered by black squares has more than 70 or more terminal hairs at each of the site locations.

From this information, one or more metric may be determined, indicating a level of hair loss or baldness for this patient. For example, one metric may be one which quantifies coverage of the body surface, for example, based on the proportion the 9×9 array which has minimal terminal hair (few than 40 terminal hairs in each identified site location), which is 27 of the 81 squares, or 33%. Indicating that 33% of the body surface is going bald. In another embodiment, the metric may be weighted to account for the difference of hair density between array 250*a* and 260*a*, providing for a metric of hair density. For example, if each white square is associated with a value of 0, each grey square is associated with a value of 1, and each black square is associated with a value of 2, the highest value which could be obtained over a 9×9 array would be a value of 162. However, the value as illustrated in FIG. 2*a* would be 81, or 50%.

As indicated earlier, FIG. 2*b* is a representation of the same body surface 200 at a second instance in time, $T_2$ For example, several months after a hair treatment has been applied, or just several month after a patient's first visit. The hair treatment may comprise, for example, the application of a hair growth enhancement product or a hair implantation treatment on the bald in the region 250*a* only. The disposition of fiducials allows for images to be acquired, or image processing to be carried out over the same area between the two instances in time ($T_1$ and $T_2$), enabling the image to be taken from the same distance from the body surface, or enabling magnification or reduction in image size accordingly so that the same areas are compared. As illustrated, at $T_2$, the subset of 9×3 squares forming the subset 250*a*, comprises grey squares, indicating in this particular example that this area now covered by each grey squares has 40-70 terminal hairs in each square. The subset of squares 260*b* also comprises grey squares, indicating in this particular example that the area covered by grey squares has 40-70 terminal hairs within each of the site locations. The subset of squares 270*b* comprises black squares, indicating as before that the area covered by black squares has 70 or more terminal hairs within each of the identified site locations.

From this information, using the same metric calculations described above, for the first metric, after application of the hair growth enhancement product or the hair implantation treatment, there are no white squares or site locations having fewer than 40 terminal hairs. Therefore, after application of a hair growth enhancement product or a hair implantation treatment 0% of the evaluated body surface of interest is going bald (for example, based on our earlier explanation when fewer than 40 terminal hairs in each identified site location being considered as "going bald"). For the second metric calculation discussed above, the weighted metric, once again the highest value which could be obtained over a 9×9 array would be a value of 162. However, the value as illustrated in FIG. 14*b* after application of the hair growth enhancement product or the hair implantation treatment is now 108 (or 67%). In either case, the metric clearly shows that there has been an improvement in the patient's hair loss condition, that his balding area (e.g., the area with fewer than 40 terminal hairs in each identified site location) has been reduced, and the amount of hair, or hair density has increased, over the time between the first and second instances, $T_1$ and $T_2$. It will be apparent to the reader that these examples illustrate only two ways in which a metric can be provided to measure baldness, but many other variations of this methodology may also provide useable metrics which are contemplated within the scope of the present disclosure.

As indicated above, the current methodology allows a complete map or metric (e.g. baldness metric or hair health metric) to be associated with a patient. In addition to providing a visual indication of the progress achieved by a procedure having been performed, the current disclosure also provides for the creation of a first file comprising data representative of one or more values associated with one or more procedure sites at a first time, creation of a second file of data representative of one or more values associated with the one or more procedure site at a second time, and determining a variation or similarity in the correlation in the data of the corresponding site locations during the first and the second time. The variation or similarity once determined may be output in a form which conveys this information on the same representation of the body surface, visually to the physician. Alternatively, the data may be saved in another file associated with the patient, to be referred to at a later date.

Figure 4:
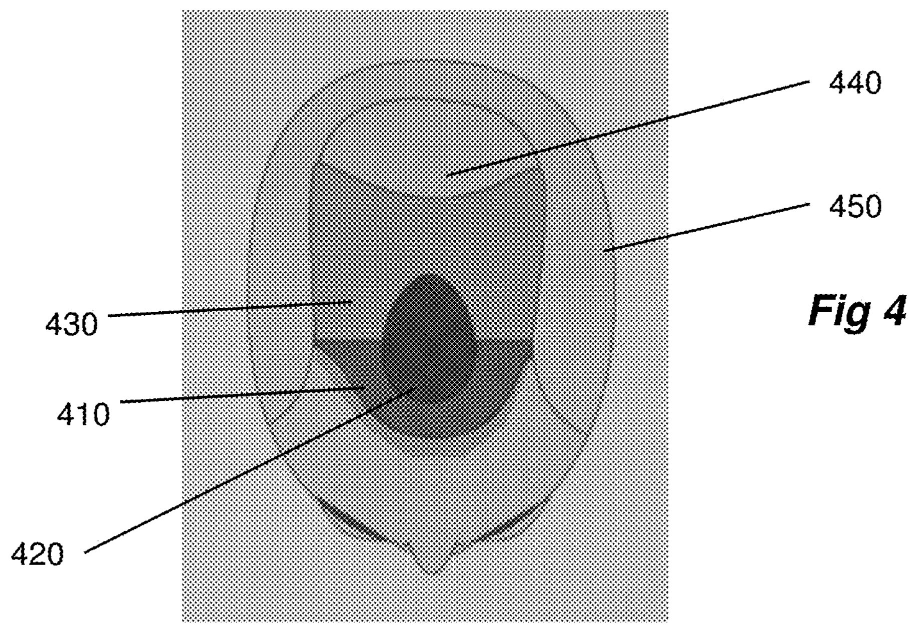
FIG. 4 illustrates examples of various regions on a scalp.

It will be appreciated that though explained in terms of an array of squares, there are many other ways in which a representation of a body surface may be divided in order to assign representations over an area, so that a metric can be applied to hair loss. For example, as illustrated in FIG. 4, a template of defined regions associated with hair loss may be utilized, and for a particular patient, a metric assigned to each of the regions. Based on experience and/or data compiled over time, a representation assignment associated with the various regions at different stages of hair loss can be determined, and utilized in providing a useful metric in terms of hair loss to individual patients. By providing such a metric periodically (for example, every six months or every year, depending on circumstances) to individual patients, a physician is able to determine whether the patient's hair loss is proceeding at a typical rate, or faster or slower than similar persons. Should the patient be experiencing a faster rate or hair loss, or hair loss of an unexpected or unpredicted distribution, the physician may be able to tailor the treatment plan accordingly. Alternatively, the unexpected or unpredicted rate or distribution may be an indication of a medical condition for which treatment may or may not be available. In some situations, the metric may provide confirmation to the patient that they are not in fact experiencing hair loss, but rather incorrectly perceive that their hair density was higher in the past.

In this manner, a metric of hair loss can be provided, enabling the patient to attain a visual understanding which may not be readily apparent by eye, and providing a quantitative measure of hair loss progression, or regression. It will be apparent that the methodologies and embodiments discussed in reference to the metric of hair loss with the aid of FIG. 1-3 may be combined with the methodologies and embodiments discussed with respect to FIG. 5, FIG. 6 or FIG. 7 below, and various combinations are contemplated.

Hair Loss Management Tool

The present disclosure also provides a methodology by which a physician can provide a patient with a personalized treatment plan, based on metrics which provide information on the classification, distribution and/or density of follicular units for the specific patient, thus providing the patient with a personalized plan based on the actual hair on his head. This aspect of the disclosure utilizes the mechanics of hair loss, determines the dynamic change in proportions of follicular units to ascertain, for example, if and/or when a hair loss treatment should be initiated to achieve more favorable results. The classes of follicular units, density and follicle size will vary according to many factors, including ethnicity, so for the purposes of discussion it will be assumed that our patient is a Caucasian male.

Human hair emerges from the scalp in groupings, which are knows as follicular units. Follicular units may be classified based on a number of hairs or hair follicles (typically 1-5) in the follicular unit. A person with a high density of hair, typically has various quantities of the following classes or types of follicular units: 5-hair follicular units (F5), 4-hair follicular units (F4), 3-hair follicular units (F3), 2-hair follicular units (F2) and 1-hair follicular units (F1). As hair loss progresses, the density of hair typically reduces, with fewer or no F5 or F4 being found, with the F5s becoming F4s, F4s becoming F3s, the F3s becoming F2s, F2s becoming F1s, and some of the 1-hair follicular units F1s falling out. In the earlier stages of hair loss, though the number of follicular units in the area may remain substantially the same, the number of hair follicles in each follicular unit may begin to decrease. As hair loss progresses, the follicular units with the higher number of hairs decrease or become zero, the follicular units with the lower number of hair increase, and eventually the number of follicular units decreases also. Though the classes of follicular units may vary according to ethnicity, the progression experienced in hair loss is the same.

Figure 5:
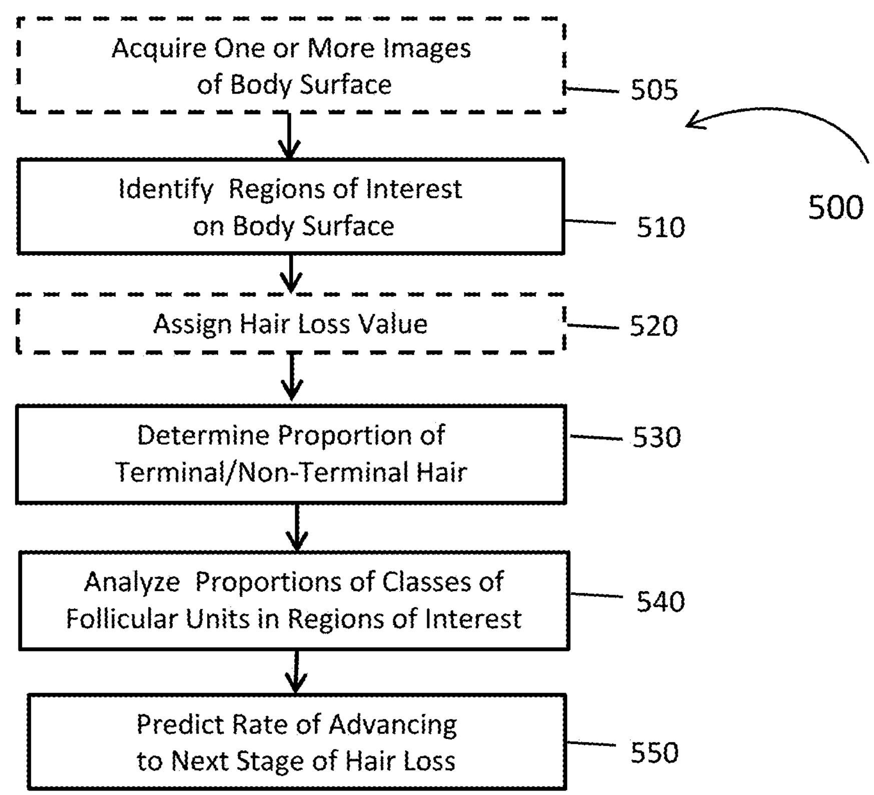
FIG. 5 is a flow chart illustrating an example of a general method for predicting a rate of advancing to the next stage of hair loss.

FIG. 5 is a block diagram illustrating an example of a computer-implemented method for determining and managing hair loss, including a general methodology 500, for predicting a rate of advancement to a next stage of a hair loss value. For example, predicting the rate of advancement of hair loss that may be accomplished in a predetermined time increments, such as 3 month increments, or other desired time intervals. A computer-implemented method illustrated in FIG. 6, may utilize some of the steps similar to those shown in reference to FIG. 5 and such method may assist in determining and planning if and when a hair transplantation procedure or other such procedure should be undertaken. Using these methodologies, a physician is able to suggest to a patient the available options, and potentially what the next step should be. Potential suggested actions may include, for example, a recommendation "to do nothing", but come back again in a few months to track progress; to commence with a hair treatment plan, such as application of an ointment or other such solution to minimize hair loss; or perhaps consider undergoing a hair transplantation, and if so, when. These methodologies determine what action to adopt with respect to the stage of hair loss, and associated hair loss factors, managing the expectation of the patient as to what can be actually achieved based on the determined rate of hair loss, and classes of follicular units available at a relevant time.

As a preliminary matter, in step 505, one or more images of a body surface may be obtained, acquiring image data, for example, by using an image acquisition or imaging device, or any other technique known in the art. In other embodiments, the image data can be created in real-time, using a digital camera. For example, in some embodiments an image acquisition device may be attached to a robotic arm. In other embodiments, the image acquisition device may be still incorporated into the automated (e.g., robotic) system but it does not have to be attached to the robotic arm. Alternatively, in further embodiments, the image acquisition device could be a device separate from the robotic system. Once an image has been acquired, one or more regions of interest, for example areas of hair and areas of bald scalp can be identified (step 510) using various methodologies, including for example, through use of segmentation, contouring, edge recognition and other known image processing techniques. In this manner, if applicable, one or more areas such as a frontal region 410, a forelock region 420, a mid-scalp region 430, a crown/vertex region 440, or a lateral fringe region 450 can be identified. In the case of a patient who is already experiencing hair loss, the identification of regions of interest may include both areas with hair (potential donor areas) and with less or without hair (potential recipient areas). For purposes of hair transplantation, typically the back of the head is utilized as a donor area, though hair may be harvested from other regions depending on the patient, and their distribution of hair. The general methodology of FIG. 5 may include an optional step 520 that may be implemented in some of the embodiments. In such optional step 520, based on the identification of a particular set of regions, as known to those skilled in the art, a hair loss value may be assigned using any appropriate technique. For example, the hair loss value may be assigned by matching the actual identified regions of a particular patient to those predetermined or otherwise known as representing a particular stage of hair loss. In one embodiment of the disclosure, the assignment of hair loss value may be based on the Norwood scale of hair loss for male patterned baldness, though other scales may be used. A pattern-matching algorithm can be used to recognize the hair pattern and match it to one of a series of images in a repository, for example, to assign a corresponding value of hair loss. In those embodiments where the value of the hair loss is assigned, such determined value may be used as described later below.

In step 530 a proportion of terminal or non-terminal hair is determined in each regions of interest. Typically, a proportion of non-terminal hair of greater than 20% is an indication that a hair loss process has started and that a person has a condition referred to as an androgenetic hair loss. In various implementations, it may be determined, for example, which hair in the region of interest or certain portion of the region of interest are terminal and which one are not, and based on that information it may be further determined the relevant proportions of either terminal or non-terminal hairs (determination of the proportion of one would simultaneously provide a corresponding proportion for the other). In other words, determining whether a condition of androgenetic hair loss exists may be done by determining either the proportion of terminal or non-terminal hairs in the area. Identification of terminal and/or non-terminal hair may be carried out by various available means, including as described earlier in reference to FIG. 1 and discussion about the metric of hair loss.

The determination of non-terminal hair (such as vellus hair, dying, miniaturized, or non-regenerating hair), is useful because it allows to establish in a first place whether a person actually experiencing hair loss, as stated above. In addition, it is useful because non-terminal hairs are deemed unrecoverable, an effect associated with male pattern baldness. Hence non-terminal hair does not need to be taken into account due to the fact that it will eventually fall-out or disappear and will not aid in the overall look achieved once a hair implantation procedure is performed, or other such treatment is applied. The classification of terminal and non-terminal hair (vellus or miniaturized) provides a means by which terminal or healthy hairs can be included to form part of the density of hairs in the region of interest, and non-terminal hairs can be excluded in the calculation of the density of hair in the region or area of interest. It will be appreciated that potential recipient areas with a higher number of terminal follicles or hair will require less implantation sites than recipient areas with a higher number of non-terminal hair, and similarly potential harvesting areas with a higher number of terminal hair will produce more donor sites and hair grafts available for harvesting. So for planning purposes, when analyzing a region of interest which is a potential recipient region or area, non-terminal hair does not need to be counted and included in the analysis of classes of follicular units as described below. Similarly, in some embodiments, the classification analysis may be performed in the regions of interest that could be used as donor areas for harvesting to predict and evaluate how much and what types of hair will be available in such potential donor area for harvesting in the future.

Typically when progressive hair loss begins, the rate at which hair will be lost will depend of various factors, some of which were discussed earlier. The natural distribution of follicular units in an average Caucasian male is approximately 20% of F1, 40% of F2, 30% of F3 and 10% of F4 and higher (F4+), with an error margin of about +/−10%. As discussed above, as hair loss progresses, the higher value follicular units disappear, and the lower values increase in numbers, until eventually they all disappear. However, people of different ethnicities may have a different typical thickness of hair, or different typical distributions of various classes of hair. For example, in an Asian population, the individual hair follicles are typically thicker than in a Caucasian population, and F4 and F5 classes of hair are rarely found, even in a healthy person who does not exhibit any hair loss. Therefore, it was discovered that the distribution of classes of follicular units in a particular person without the knowledge of what represents a terminal hair for such person and whether the hair loss process has started, may not by itself provide an accurate picture of the state of the hair health or hair loss. Therefore, determining the proportions of terminal and non-terminal hair (and hence, whether the hair loss begin to occur) may provide a point of reference and improves the accuracy of the analysis of the distribution of classes of the follicular units as further described. For example, presence of hairs or follicles of different caliber is typical of androgenetic alopecia and reflects progressive hair miniaturization due to the disease. A diversity of greater than 20% of hair caliber is diagnostic of androgenetic alopecia.

Having determined the proportion of the terminal or non-terminal hair in step 530, the follicular units in the regions of interest (for example, regions that may be identified as potential recipient areas) are analyzed in step 540. The analysis 540 may comprise segmenting the image of the recipient area to recognize the hair, as well as using various known image processing techniques, for example edge detection, object recognition and selection. In step 540, a proportion of follicular unit belonging to each of the types or classes (e.g., F1 to F5) in the areas of interest, for example recipient areas, may be analyzed, with analysis comprising identifying the classification, or classes of the follicular units, identifying the caliber of the hairs, adjusting the classification of follicular units based on the caliber of hairs to account for hair which is non-terminal, and determining a follicular unit distribution over the area of interest. Assuming that the determined proportion of non-terminal hair was less than 20% or the determined proportion of terminal hair is 80% or above (within the norm), and if the analysis of follicular units described in step 540 above reveals that four or more types or classes of follicular units were present, (that is comprising F1s, F2s, F3s and F4+s) and that their distribution was approximately 20% of F1s, 40% of F2s, 30% of F3s and 10% of F4+s, +/−10%, such area (of the region of interest) would be identified with a high score and ranked, for example, as an A-type area. The A-type area would denote a healthy or stable region that is not associated with a progressive hair loss, and unlikely to require a hair implantation any time soon, or at least, for example, in the next 12-36 months. Should the same potential recipient area have a proportion of non-terminal hair of greater than 20% (or terminal hair less than 80%), and comprise substantially only three types or classes of follicular units, that is F1s, F2s, and F3s, with a negligible quantity of F4 or higher follicular units, for example 22% of F1s, 44% of F2s, 33% of F3s, and only 1% or less of F4, this would correspond to a lesser score, ranked for example as a B-type area and denoting a region or area which was showing signs of hair loss, with a slight reduction of hair density. This type of area may be indicative of one that is somewhat likely to benefit from a hair implantation, for example, within a time frame of 12-24 months, or a longer period, as may be appropriate under circumstances. Likewise, should it be determined that proportion of non-terminal hair was greater than 20% or the determined proportion of terminal hair is 80% or less and the potential recipient area comprise substantially only F1s and F2s, with a negligible or no quantity of F4+, and a significantly reduced proportion of F3 (a reduction of 30% or more), for example 31% of F1s and 63% of F2s, 5% of F3, and 1% or less of F4, it would correspond to a C-type area, denoting a region which was showing a more pronounced sign of hair loss. Such C-type area may indicate that it is likely that the area would benefit from a hair implantation, for example, within a time frame of 9-18 months, or in some cases 3-6 months, or other appropriate time frames. Finally, should the same potential recipient area have a proportion of non-terminal hair of greater than 20% (or terminal hair less than 80%), and a recipient area comprise substantially only F1s and F2s, with a negligible quantity of F3 and no F4, for example 65% of F1s and 34% of F2s, and 1% or less of F3, it would correspond to a D-type area, denoting a region which may benefit from a hair implantation, for example, within a time frame of 6-12 months, or even sooner, for example within the next 3 months. Therefore, based on the above analysis of the proportion of non-terminal or terminal hair and the distribution of various classes of follicular units enables a prediction of advancing to the next stage of hair loss to be determined. In one embodiment a prediction of hair loss may be determined for example, based on a higher proportion of lower classes of follicular units, and the lack of higher classes of follicular units. Moreover, based at least on two (or more) measurements on the same patient made at two points in time separated by a predetermined amount of time (for example, 3 to 6 months, however, any other appropriate time frame may be used depending on a particular case), one may determine a rate of advancement of the hair loss. Furthermore, based on the known statistics and historic data for various types of patients (with reference, for example, to ethnicity, age, race, etc.), a prediction may be calculated and made with respect to the rate of advancement of the hair loss for a particular patient. Also, a combination of the historic data with the at least two spaced apart in time measurements for a particular patient may be used in determining a rate of advancement of hair loss. For example, Patient 1 and Patient 2 (both with the same original distribution of the classes of hair at the time of first measurement) at the time of the second measurement showed the following results: Patient 1, a Caucasian male, had 60% of F1s and 40% of F2s, and no F3s or F4s and Patient 2, also a Caucasian male had 40% of F1s, 50% of F2s, and 10% of F3s, with no F4s. As a result of comparison, one could determine that the hair loss of Patient 1 was progressing to the next stage of hair loss faster than the hair loss of Patient 2 Based on data from previous patients, in some embodiments, the physician may be able to predict a time for the progression of such hair loss. In other embodiments, the proportion of follicular units, in combination with the density of hair follicles within a predefined region, may enable a determination to be made as to the rate of hair loss. For example, in a case of Caucasian male, with 60% of F1s and 40% of F2s, and no F3s of F4s, and the total number of hair follicles being less than 50 hairs per $cm^2$, one could determine that the patient's hair loss was progressing such that the next stage of hair loss would be reached within a time frame of approximately a year. For the same patient, should the total number of hair follicles be more than 100 hairs per $cm^2$, one could determine that the patient's hair loss was progressing such that the next stage of hair loss would be reached a longer time frame of, for example a 2-3 year time frame.

This information ultimately providing data for planning if and/or when to undergo a hair treatment plan, or if and/or when to undergo a hair transplantation procedure. As will be appreciated by those skilled in the art, in various implementations and depending on a particular patient, a different number of area types A, B, C etc. may be defined, as well as the particular characteristics of each such area. Similarly, different ranges of the suggested time frames for performing treatment may be associated with each such defined type of area A, B, etc. Also, in some embodiments, where the hair loss value was assigned during the process, the method may further comprise a step of predicting and reassigning the value of hair loss as of a future date based on the predicted rate of advancing of hair loss.

According to another aspect of the disclosure a rate of progression, advancement or even regression of hair loss can be determined, the rate determined by carrying out the methodology illustrated in FIG. 5 two or more times over an extended period of time, the time being from 6-24 months, for example.

Figure 6:
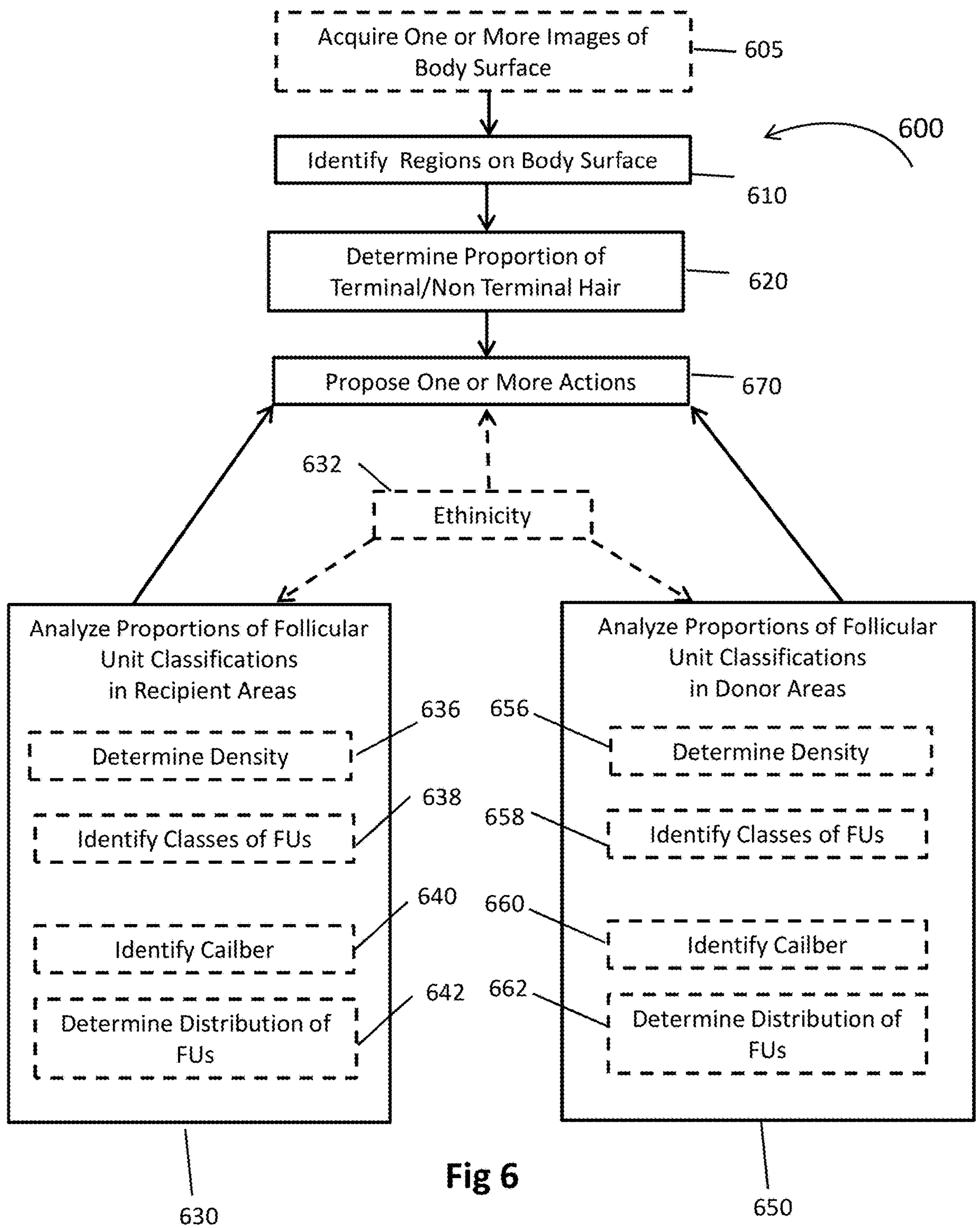
FIG. 6 is a flow chart illustrating an example of a general method for managing hair loss, including proposing one or more actions or treatment options and/or the timing of such treatment options.

FIG. 6 is a block diagram illustrating an example of a computer-implemented method for analyzing the existing proportion of hair types on a body surface to plan and manage potential treatments and the expectation of a result that can be achieved by such treatment, including if and when the hair transplantation procedure should be undertaken. It will be apparent that many of the steps of FIG. 5 may be implemented in the methodology of FIG. 6.

As a preliminary matter, in step 605, one or more images of a body surface may be obtained, acquiring image data, for example, by using an image acquisition or imaging device, or any other technique known in the art. Once an image has been acquired, regions of interest, for example areas of hair and areas of bald scalp can be identified (step 610) through use of segmentation, contouring, edge recognition and other such known image processing techniques. Having determined proportions of terminal and/or non-terminal hair in relevant regions of interest (step 620), the follicular units in the regions identified as potential recipient areas and potential donor areas are analyzed (steps 630 and 650 respectively).

The analysis 630/650 comprises determining a distribution of follicular units found in each of the respective potential recipient and donor areas. The analysis 630/650 may comprise one or more of the modules identified by dotted lines, with the particular results from each module contributing to the one or more actions that can be proposed in module 670. In some instances, certain of the one or more modules may have a greater contribution to the one or more actions proposed in 670, implemented by a weighting factor. In some embodiments, the analysis of 630 and 650 may require entry in step 632 of the ethnicity of the patient, as classes of follicular units, density and caliber, for example, vary according to ethnicity. Various steps of the analysis of 630 and/or 650 may be implemented using various image processing techniques, including, for example, image segmentation. Some of the Examples of modules that may be used in the analysis 630 or 650 include determination of density (636,656), identifying classes of follicular units (638, 658), identifying hair caliber (640, 660), etc. In reference to the optional module of identifying hair density, the results of such density determination may dictate if certain treatment plans are an option. For example, if it is determined in step 656 that there is insufficient density of hair in a donor region to harvest for subsequent implantation, this determination will result in the methodology determining an option other than suggesting a hair transplant to the patient. Hair transplantation cannot be recommended as an option to a patient with insufficient density of hair in a donor region, as further depletion of hair in this region will only increase the appearance of baldness in that region. For example, some physicians consider that a density of fewer than 20 grafts in a 1 $cm^2$ area or an average of 40 hairs per 1 $cm^2$ area (assuming that F2s to be an average), is too low for hair transplantation to be an option.

In some embodiments, analysis may comprise identifying the classification or classes of the follicular units (steps 638/658), and identifying the caliber of the hairs (steps 640/660). The result of the identification of terminal and non-terminal hair (step 620) may additionally be used in the determination of density (steps 636/656), with terminal hair being used to calculate the density of hairs in the recipient region, the non-terminal hairs being excluded in the calculation of the density of hair in the recipient region. Additionally, the result of the classification of terminal and non-terminal may be utilized in adjusting the classification of follicular units, accounting for hair which is non-terminal based on the caliber of hairs. In one embodiment this may comprise determining a number of follicular units in each class taking into consideration existence of terminal and non-terminal hair, wherein each class is based on the number of hair follicles in a follicular unit. In step 642/662, the follicular unit distribution over the recipient/donor areas may be determined.

An example of the determination of the distribution of follicular units over the recipient areas was discussed above in reference to FIG. 5. In a similar manner, if it were determined that four or more classes of follicular units were present in a donor area of region of interest and that the distribution of follicular units was approximately 20% of F1s, 40% of F2s, 30% of F3s and 10% of F4+s, +/−10%, assuming that miniaturization was less than 20%, then such donor area would be ranked with a high score, for example as an A-type area, and denoting a region which did not appear to be moving to the next lower stage of hair loss value, thus providing a good resource as a potential donor area. Should the same potential donor area comprise substantially only three follicular unit classification types, that is F1s, F2s, and F3s, +/−10%, with a negligible quantity of F4+, for example 22% of F1s, 44% of F2s, 33% of F3s, and 1% F4, and a proportion of non-terminal hair of greater than 20% (wherein an increase of non-terminal hair sometimes may be referred to as miniaturization), this would correspond to a lesser score, ranked for example as a B-type area, denoting a region which was showing signs of hair loss, and a slight reduction of hair density. Such region may be automatically ranked by the system as possible but less favorable choice for a donor area, giving priority for potential future harvesting to the region ranked as type A. Of course, if desired, such automated order of preference may be adjusted or overridden by the user if some other additional considerations make this type B area a better region for potential hair harvesting than the region ranked as A type based on the above analysis. In another example, should same potential donor area comprise substantially only F1s and F2s, +/−10%, with a negligible quantity of F4+ and a significantly reduced proportion of F3 (a reduction of 30% or more), for example 31% of F1s and 63% of F2s, 5% of F3, and 1% of F4, it would correspond to a C-type area, denoting a region which showing more significant signs of hair loss, and therefore, not necessarily a good donor area. In fact, as a result of the analysis according to the methodology of FIG. 6, such initially identified potential donor area may be reconsidered as potential recipient area. Finally, should a donor area comprise substantially only two follicular unit classification types, that is F1s and F2s, with a negligible quantity of F3 and no F4, for example 65% of F1s and 34% of F2s, and 1% of F3, it would correspond to a D-type area, denoting a region which should not be chosen as a donor area. It should be noted that the above examples are based on a Caucasian male patient. Should the ethnicity differ, being Asian, for example, a distribution of only F1s and F2s in the region of interest while the proportions of the terminal hair correspond to the typical standard numbers for healthy hair, as a result of the analysis such region may be identified as the type A or B and utilized as donor area, since this particular ethnic group generally has a lesser occurrence of F3 and F4.

Having determined whether conditions of beginning of hair loss are present in step 620 (for example, by determining proportions of the terminal and/or non-terminal hair), and subsequently analyzed the proportions of classes of the follicular units in each of the donor and recipient areas, step 670 of the method may propose one or more actions that may be available to the patient, suggesting, for example, the most suitable options available based on the data collated, including the distribution of follicular units in both the recipient and donor areas. In this manner, by proposing one or more actions, the physician is able to manage the expectation of the result that can be achieved by, for example, suggesting which region of the scalp it is recommended that hair be implanted into, such as a hairline, or the mid-scalp area, to perhaps achieve the best distribution of hair over the recipient and donor areas, given the limited supply of donor hair. As discussed above, this determination may be based on the identification of follicular units, hair density, hair caliber, determining a proportion of miniaturization, adjusting the follicular unit classification to account for non-terminal hair (such as taking into consideration existence of terminal and non-terminal hair when determining the class of follicular unit, each class based on a number of hair follicles in a follicular unit), and the distribution of follicular units within the donor and recipient areas. The compilation of all this information ultimately serving as data for planning if and/or when to undergo a hair treatment plan, or if and/or when to undergo a hair transplantation procedure. In some embodiments, an initial hair loss value may be assigned to the scalp and this information may be also taken into consideration in the above determinations and decisions. It will be apparent that the system and tools used in performing the methodology described may be customized and configured such that the software may be tailored to incorporate a physician's preference as to what action be taken, what options should be suggested, and when such action should be performed. Such customization may be based on a physician's particular experience, existing data, the physician's practice capabilities, and/or any combination of the above. In an alternative, a pre-configured set of determinations may be utilized and presented in an automated manner. The system may be further configured to allow the user to modify or override any automated options proposed by the system.

Some examples of how an automated system may be configured or programmed to provide automated determinations are provided below. It should be understood that many alternative implementations are within the scope of the present disclosure.

Assume that the density of hair in the recipient areas is less than 50 hair per $cm^2$, and that it is determined in step 630 that the distribution of follicular units in the recipient areas is approximately 70% of F1s and 30% of F2s, so that the recipient area is characterized as a D-type area. Based on this information, one would assume that hair transplantation should be recommended. However, if step 650 should determine that the distribution of follicular units in the donor area(s) is approximately 65% of F1s and 34% of F2s, and 1% of F3, also corresponding to a D-type area (no sufficient donor area available for harvesting), the system may determine based on the results of steps 620, 630 and 650 that, for example, no hair transplantation should be considered by the patient due, primarily, to the lack of hair in the donor area. The corresponding analysis and logic may be programmed into the decision tree for the automated determination and proposal of potential options.

Similarly, if in step 620 it is determined that the proportion of non-terminal hair is greater than 20% (an indication of androgenetic hair loss), and in step 630 that the distribution of follicular units in the recipient areas was approximately 70% of F1s and 30% of F2s, corresponding to a D-type area, from the data provided by step 630, once again one may assume that a hair transplantation should be recommended. Then, if in step 650 it should be determined that the distribution of follicular units in the donor areas is approximately 20% of F1s, 40% of F2s, 30% of F3s and 10% of F4, (with a density of 60 hairs per $cm^2$ or more) corresponding to a A-type area, such donor are will be identified as an acceptable donor area. The system may be programmed accordingly such that the compilation of steps 620, 630 and 650 results in a determination that a hair transplantation should indeed be considered by the patient. Should such determination be made, the system may additionally be configured to indicate to the physician and the patient the time frame of taking such action. For example, in this instance, assuming once again that the proportion of non-terminal hair is less than 20%, since the donor area is an A-type area, the system may be configured to recommend that the patient may undergo hair transplantation, for example, right away or that they can wait (for example, up to 1 year), because the donor area has sufficient hair and does not exhibit the symptoms of hair loss. However, should the distribution of the various classes of follicular units in the donor area be 22% of F1s, 44% of F2s, 33% of F3s, and 1% of F4, indicating a B-type area, the system may be configured to recommend that the patient undergo a hair transplantation sooner (e.g., within a two-year time frame), to ensure that sufficient donor hair would still be available to harvest and implant into the recipient areas in light of the fact that such donor area already began to show the symptoms of hair loss.

The examples above provide only samples of various configurations to provide automatic determination of an action to take (or options suggested), and a time frame in which to take it, based upon the input from an analysis of the proportions of classes of follicular units in the donor areas, an analysis of the proportions of classes of follicular units in the recipient areas and determination of whether the androgenetic alopecia is present in a particular patient (for example, by determining proportions of the terminal or non-terminal hair). It will be appreciated that the results of steps 620, 630 and 650 can be combined to create an array of pre-selected actions to take, the actions including, but not limited to initiating use of a topical hair enhancement product or treatment, hair growth stimulation product, undergoing hair transplantation, shaving one's head, or considering a wig. In addition, associated recommended time-frames in which to take such action may also be provided. It will be appreciated that based on the results of the steps 620, 630 and 650, only certain options will be allowed to be proposed as actions in step 670. For example, as discussed above, if there is an insufficient density in the donor areas, for example, hair transplantation may not be an option, even though the analyzed proportions in the recipient region may be suggesting that action to be an option. In other instances, hair transplantation may be an option, but the number of regions into which hair may be implanted may be constrained by the availability of proportions of follicular units available. In yet other situations, a determination of a density in the potential recipient area of less than a predetermined number of hair follicles or hair grafts per unit area (for example, 40 hair follicles per 1 $cm^2$), may dictate that a hair transplantation automatically be considered as an option.

Consider a Caucasian male patient who comes to see his physician explaining that hair loss runs in his family, and that he wants to have a hair transplant. If the patient appears to have a full head of hair, with no noticeable reduction of density in any of the regions, even though the physician is aware that no hair transplant is needed at this stage, the physician may still utilize this methodology to provide a reference, a baseline to which future hair loss can be compared. Such methodology may be very useful, for example, to patients with the family history of hair loss since the chances of this particular patient needing hair transplantation at some point is relatively high. In this particular case, even no treatment is suggested during the initial patient consultation, due to the patient's family history, it may be suggested that the patient return in 12 months to check if there has been any change in his situation.

Should the same patient return in 6 months or other suggested time, after noticing that he can see significantly more scalp that usual in the mirror, and has been picking up substantially more hair from the shower, the physician may once again utilize the methodology disclosed. It may be found, for example, that applying the methodology this time determines in step 620 that the proportion of the terminal hair is now reduced, that the distribution of follicular units in the donor regions (step 650) is approximately 20% F1s, 40% F2s, 30% F3s and 10% F4+s, and the distribution of follicular units in the recipient regions (step 630) is approximately 31% F1s and 63% F2s, 5% F3, and 1% F4. Though this example is somewhat extreme, it will be apparent that the patient has experienced severe hair loss over a short period of time (the physician has the results from the session 6 months ago to refer to). According to the methodology described herein, analysis of the results of steps 620, 630 and 650 this time will likely lead to recommending some type of testing to discover the reason for such accelerated hair loss and eventually an appropriate treatment, including, for example, a hair transplantation within a short period of time before the density of the donor area is reduced more. Of course, it will be appreciated that this may be one of several suggested actions, each with potentially different results. However, based on the information of proportions of follicular units available in the donor regions, the proportions of follicular units in the receiving regions, and the identified miniaturization and density, the physician will be able to manage the expectation of results attainable based on the client's specific hair proportions and analysis.

Analysis of Hair Growth Phases to Determine the Timing and which Hair to Harvest and Implant It is known that the hair in its life cycle goes through several physiological phases of hair growth. The anagen phase is the first phase of the hair cycle during which new hair is growing and the hair follicle is elongating. The hair follicle actively produces the hair shaft (hair shaft production). This phase is the longest of the hair cycle typically 3-10 years for the human scalp, with the duration of the anagen phase responsible for determining the length of the hair shaft. Due to the high mytotic rate of follicular matrix cells, the anagen phase is very sensitive to noxious insults. Approximately 75%-95% of hair follicles in the scalp of a healthy person are normally in the anagen phase.

Catagen is the second phase of the hair cycle, a brief portion in the hair cycle when the hair growth stops and hair transitions to a resting period. This is a transitional phase which typically lasts 2-3 weeks and is characterized by apoptosis of the hair matrix cells and involution of the lower part of the follicle. During catagen phase, the hair bulb migrates up from the hypodermis to the mid-dermis. Telogen, the final phase, (resting phase) is the part of the hair cycle that follows the catagen phase. During this phase hair shaft production is absent and the hair bulb is completely keratinized. The telogen phase, in the scalp follicles, lasts about 3 to 4 months but it is considerably longer in other body regions such as the lower limbs. The hair shaft remains anchored to the follicle during the telogen phase.

U.S. Pat. No. 6,985,611 is an example of state of knowledge, which describes how to simulate the chronological evolution of a scalp over time. The present disclosure teaches novel methods and device for planning various procedures and treatments (such as hair transplantation procedures and hair loss treatments), including determining the timing of such procedures and treatments and even how and which hairs to select for harvesting and subsequent implantation, based on the understanding of the evolution of the hair growth phases over time, as described below.

A comparison of the anagen versus telogen hairs on the scalp is indicative of the health of the hair, with a healthy scalp having approximately 75% to 95% of the hair in the anagen phase. Hair in the anagen phase grows at approximately 0.35 mm per day (1 cm per month). Telogen hair does not grow. If less of a proportion of the hair is in the anagen phase, this may be an indication of a condition called telogen effluvium which has multiple causes. These causes include, but are not limited to, the condition being due to: 1) a normal variant, 2) due to hormonal abnormalities (e.g. hypo/hyper thryroidism, hyperandrogenism, vitamin D or E deficiencies), 3) due to hyper-vitamin A, 4) due to iron deficiencies, 5) due to inflammatory disease, 6) due to hyperprolactinism or other ailments. Understanding which hairs are in which hair growth cycle (and especially identifying hair in the anagen growth phase) is useful in planning hair transplantation, according to the present disclosure. By selecting particular follicles to harvest and implant based on their hair growth phase, or by choosing a timing of the procedure or treatment based, for example, on the overall condition of the hair growth phases of the hair and the distribution over the relevant surface of the hairs in different hair growth phases, a more successful outcome may be realized, and a cosmetic impact after hair transplantation to be realized sooner.

Figure 7:
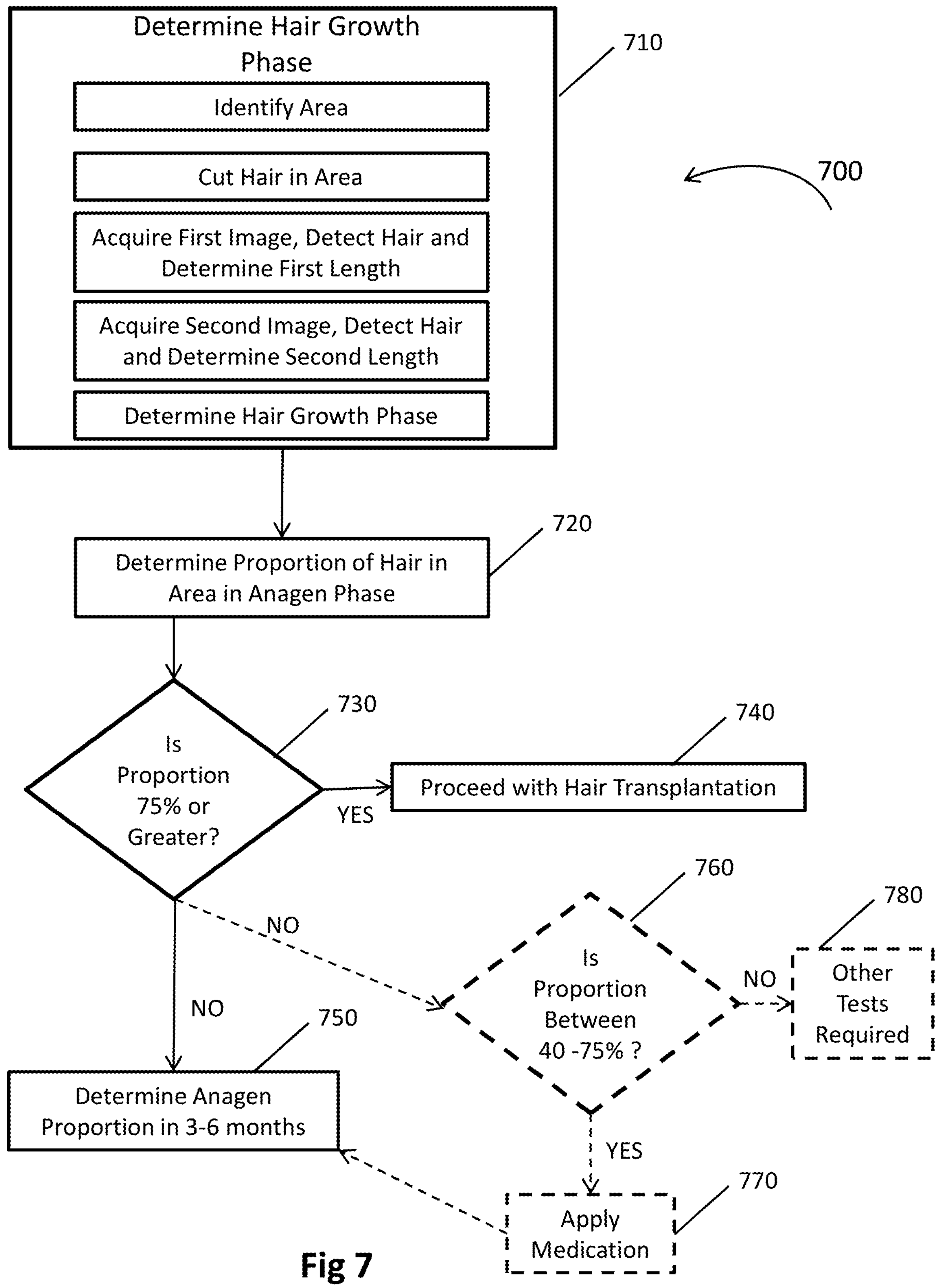
FIG. 7 is a flow chart illustrating another example of a general method for managing hair loss, including determining a phase of the hair growth and the action to take based on the proportion of hair in the determined hair phase.

In one aspect of the disclosure, as illustrated in FIG. 7, prior to undergoing a hair transplantation procedure, the proportion of hair in the anagen growth phase is determined. This determination may be made first determining how much hair in the region of interest is in each of the hair growth phases, as shown in step 710. This step may be accomplished by various methodologies, including those described in the U.S. Pat. No. 6,985,611 incorporated herein by reference. For example, in some embodiments the step 710 may comprise the following:

1) As a preliminary step, identifying a region of interest, such as an area on the body surface, comprising hair. Such area may have a diameter of 1 cm, for example.

2) As another preliminary step, cutting a population of hair in this area or region of interest to a predetermined length, approximately 0.5 mm-1.0 mm in length.

3) Acquiring a first image at a first moment in time, for example, by means of an imaging system, detecting hair and determining a first length of each hair of the population of hair within the area that was cut. The first length is determined, for example, from the point at which it emerges from the body surface to its tip (proximal to the body surface).

4) At a second moment in time, for example one to three days from the first time, the same area is re-imaged, providing a second image, hair detected and a second or new length determined for each hair in the area (the length determined in the same manner as previously).

5) Automatically comparing a first length of a hair at a first moment in time to a second length of the hair at a second moment in time and repeating the comparison for a plurality of hairs in a region of interest. Such comparison may be done, for example, by means of an algorithm executed by a processor. Based on the comparison of the second length to the first length, classifying the phase of hair growth for hair in the area (in some implementation it could be for each hair in the area, in some only for a certain representative number of hairs in the area).

In one embodiment, classification of hair to be in an anagen growth phase comprises hair that has grown more than 0.25-0.45 mm per day, for example 0.33 mm per day, during the first and second time. Hair that has not substantially grown comprises hair in a telogen growth phase. Therefore, in one example, if the time between the first and second images being acquired is 3 days, anagen hair would be identified to be the hair that had grown about 1 mm over the 3 day period of time. Such classification may be done automatically, for example, by a processor.

Having determined which hairs of the population of hair in the area are in the anagen growth phase, in one aspect of the current disclosure, a determination is made of the proportion or percentage of hair within the area that is in the anagen phase, step 720. If it is determined (step 730) that the proportion or percentage of hair within the area that is in the anagen phase is 75% or greater, such a patient is a preferred candidate for hair transplantation, the hair transplantation procedure can proceed, and a date for the procedure may be scheduled, for example, to be within a year, or within 3 months, or any other appropriate time frame. In some embodiments an indication of such may be relayed to the operator (step 740), on a display screen, for example. The determination to proceed with the procedure as well as the proposed timing of the procedure may be automatically proposed by the system (based, for example, on the pre-programmed information), or it may be selected by the user (physician) from the several options available through the user interface, or it may be chosen directly by the physician. Hair that is harvested during its anagen phase for subsequent implantation in a hair transplantation will have a higher chance of growing post-transplantation, and therefore, aid in a successful hair transplantation and achieving desired aesthetic outcome.

If, however, a patient undergoes the above analysis, and it is determined at step 730 that a proportion of less than 75% of the hair population in the area is in the anaphase growth phase, a determination would be made that such a patient should not proceed with a hair transplantation at this time, and such determination may once again be relayed to the operator, on a display screen. With this determination, there are several options that may be considered. One such option is for the patient to be advised be undergo the anagen/telogen/catagen growth phase analysis again after an appropriate time has passed, for example within a time-frame or period of 3 months to 6 months (step 750). As indicated earlier, hair which is in a telogen growth phase takes approximately 3 months to pass through this phase, and enter the anagen growth phase again. After the 3-6 months period has passed, the patient would under the analysis again, in the hope of a determination being made of a proportion of 75% or greater of the hair in the area in the anagen growth phase, and hence being able to proceed with a hair transplantation process. In another option, the determination may depend upon the actual proportion or percentage of hair in the area that is in the anagen growth phase. For example, a determination may be made if the proportion or percentage of hair in the area that is in the anagen growth phase in the range of 40-75% (step 760), should the result be positive, a determination may be made that during the next 3-6 months, prior to the next analysis being carried out, the patient should apply a medication, a hair growth stimulant, such as Minoxidil or Finasteride (770), and then determine the proportion again in 3-6 months. In the event that the result is negative, meaning that the proportion or percentage of hair in the area that is in the anagen growth phase is less than 40%, it may indicate that the patient has some potential health issues and a determination may be made that additional tests are required (780) to find out why the percentage is so low and discover the cause of the issue. For such a patient, hair transplantation or topical medications may not be a sufficient option. For such a patient, the information attained may dictate that other tests be required in order to find out why the proportion of hair in the anagen growth phase is so low, and potentially identify a medical condition the patient may have.

In this manner, based on the proportion or percentage of hair in the area that is in the anagen growth phase, a determination may be as to the best time for a patient to have a procedure, the best time defined as the time which will most likely result in a successful procedure. Based on the proportion of hair the anagen growth phase, a determination may also be made to exclude a patient from being a candidate for a hair transplantation.

In a further aspect of the current application, a determination of which hair are in the anagen hair growth phase may also be utilized during the actual hair transplantation procedure. During the hair transplantation procedure, the image processing unit may be configured (for example, with algorithms) such that once anagen hair have been identified (a proportion that will be greater than 75%, but less than 100%), the system can be configured such that only hair determined to be in the anagen growth phase is selected to be harvested for transplantation. However, since hair is harvested typically as a follicular unit and several follicles within such unit may be in different hair growth phases, some alternative approaches may be following. For example, in one embodiment, if it is determined that a proportion of greater than 75% of the hair follicles is in the anagen growth phase, there is a high probability that as follicular units are harvested, the majority of the population of follicles harvested will end up being in the anagen growth phase. Alternatively, for a multi-follicle follicular unit, should only one of the hair follicles within the follicular unit not be in the anagen growth phase, the system may be configured to harvest that particular follicular unit. Should on the other hand, more than half of the hair follicles within the follicular unit not be in the anagen growth phase, the system may be configured not to harvest that particular follicular unit. In other embodiments, the decision on which follicular units to harvest may depend upon the type of class of follicular unit. For example, if a F2 comprises one hair follicle that is not in the anagen growth phase, it may be determined that such follicular unit will not be harvested. On the other hand, if a F3 comprises one hair follicle that is not in the anagen growth phase but the other two follicles are, it may be determined that the entire follicular unit be harvested. However for a F3 comprising two hair follicles that are not in anagen growth phase, it may be determined not to harvest any part of that follicular unit at all. These various scenarios may be programmed such that the system may automatically determine which hair to harvest, or the user may make an appropriate selection using user interface.

To aid in easily identifying and indicating to the physician (or other user) those hairs that are in anagen state, a further aspect of the disclosure provides a method and corresponding device by which the proportion of hair that is determined to be in the anagen growth phase may be assigned a representation and an image of the predefined region, for example, populated with the assigned representation (similar to that described with references to FIG. 1 above). Such a method for using analysis of hair growth phase to plan hair transplantation, may comprise: identifying one or more hair follicles within a predefined region on the body surface; determining a type of hair growth phase for the one or more hair follicles; determining a proportion of hair in the anagen hair growth phase; assigning a representation to and populating the predefined region with only those representations corresponding to hair in an anagen hair growth phase; and planning a hair transplant procedure based at least in part on the determined proportion of the anagen hair and/or on a distribution of the populated representation. Planning may comprise determining when to undergo a hair transplantation procedure and/or which hair to harvest during the transplantation. The representations may also aid in providing a metric, providing not only an indication of the proportion of hair in the anagen hair growth phase, but also their distribution throughout the predefined area (or area of interest). Such metrics may be utilized for example, to provide an indication of the size of a hair harvesting session, which will be based, for example, on the number of hairs that can be harvested without compromising the remaining density of hair according to the determined distribution of hair in the anagen phase, and further based on that the number of sessions that may be required and how far apart such sessions will be scheduled based on the available hair in the anagen phase.

In some embodiments, only a sample area of the body scalp will typically be analyzed in the manner described above. In these embodiments, assuming that from the sample it is determined that the proportion of hair in the anagen growth phase is greater than 80%, the system may be configured by means of algorithms in the image processing unit to specify that hairs of less than 40 microns in caliber (vellus hair) and hair that is not greater than, for example, 0.8 mm in length does not qualify to be harvested. Such approach would allow selecting only hair that hopefully meets the criteria of being more than 40 microns in caliber and great than 0.8 mm in length, hence more likely to be in the anagen growth phase, and excluding hairs that do not qualify. In this manner, the sample area can be utilized to predict the proportion of hair in the anagen growth phase throughout the rest of the relevant body surface.

In a further aspect of the disclosure, there may be circumstances in which even though it may be preferable that hair be harvested when 75% of the hair population in the predefined area is in the anagen hair growth phase, transplantation of at least some of the anagen hair still be performed. Such circumstances may include, though are not limited to, situations in which it is determined that the patient's hair loss is progressing at a significant rate (for example, based on performing the methodologies described earlier in reference to determining terminal and non-terminal hair). For example, the methodology discussed in reference to FIG. 7 may be combined with any of the methodologies discussed in reference to other embodiments of the present disclosure. Perhaps, identifying proportions of the terminal and non-terminal hair follicles (and/or analyzing the rapid negative change of such proportions over a short period of time) may indicate that the patient may rapidly lose a significant amount of hair, including many healthy hairs that are currently available in anagen state. Under these circumstances, the physician may consider it in the patient's best interest to select hair in the anagen hair growth phase from the determined proportion, even though it is less than 75%. Therefore due to limitations imposed such as time constraints, there may be situations in which the 75% be modified to a lower value.

In accordance with various embodiments of the application, a system for planning a procedure for transplantation of follicular units in a body surface (e.g., a scalp) of a patient may comprise a user interface, processor (e.g., software-controlled), a monitor, and at least one input device. These components are common to virtually all modern computer systems, whether a stand alone (e.g., "personal") computer system, or in a system employing a centralized server with multiple remote terminal(s). It will be appreciated that embodiments of the planning system are preferably (if not exclusively from a practical point of view) software implemented, and may be run on any computer system having the basic components (processor, monitor, input device), so long as such computer system is equipped with sufficient available memory and an appropriate graphic generation and display capability. The computing system may include one or more processing units, one or more non-transitory storage media (which may take the form of, but is not limited to, a magnetic storage medium; optical storage medium; magneto-optical storage medium; read only memory; random access memory; erasable programmable memory; flash memory; and so on), and/or one or more input and/or output components for transmitting output to and/or receiving input from one or more other components (such as one or more displays, touch screens, keyboards, mice, track pads, track balls, styluses, pens, printers, speakers, cameras, video cameras, and so on). The processing unit may comprise one or more modules to execute instructions stored in the storage medium in order to perform one or more computing device functions, such as one or more treatment planning methods. The system or the processing unit may additionally include an image repository, the image repository comprising templates, images of one or more patients and/or images of portions of templates or patients. The system can be configured to implement all the methodologies, processes and techniques described herein. In another embodiment of the disclosure, the modules may be executed to run on handheld devices, for example mobile phones, smart phone, or other such devices which are also able to capture images of the body surface, taking the form of an application to downloaded onto the phone by the user.

Although it may be suggested that the computing system include particular components arranged in a particular configuration, it is understood that this is for the purposes of example. In various implementations, the computing system may include any number of computing system components (such as one or more busses, displays, networking components, dedicated image processors, co-processors, memories, hard drives, ports, graphics adapters, and so on) arranged in different configurations without departing from the scope of the present disclosure. For example, in one or more implementations the computing system may include multiple cameras and/or video cameras arranged to capture images and/or video of the same scene. By way of another example, in various implementations the computing system may include one or more interfaces for controlling machinery such as automated and/or computer-assisted surgical machinery.

It will also be appreciated that embodiments of the application may be implemented over the internet, e.g., with a user of such system employing his or her home computer as at least a part of the user interface (monitor and input device) that interacts with a remote server or computer. In such an internet-based planning system, the software that implements and controls the user interface may reside in whole or part on the user's computer or on the remote server/computer, preferably transparent to the user. In one such embodiment, the remote server downloads one or more software modules to the user's computer for temporary or permanent use.

It is to be understood that other embodiments than those described above may be utilized and structural or logical changes may be made without departing from the scope of the present application. The Detailed Description, therefore, is not to be taken in a limiting sense, and the scope of the present application is defined by the appended claims. It will also be apparent that although the methodology described above as discrete steps, one or more steps may be combined or even deleted, without departing from the intended functionality of the embodiments of the application. It will also be apparent that the methods described above may be performed manually, or they may be partially or substantially automated, including performed using robotic systems.

It will also be appreciated that the foregoing illustrated and described embodiments of the application are susceptible to various modifications and alternative forms, and it should be understood that the applications as generally disclosed herein, as well as the specific embodiments described herein, are not limited to the particular forms or methods disclosed, and that many other embodiments are possible within the spirit and the scope of the present applications. Moreover, although individual features of one embodiment may be discussed herein or shown in the drawings of the one embodiment and not in other embodiments, it should be apparent that individual features of one embodiment may be combined with one or more features of another embodiment or features from a plurality of embodiments. By way of non-limiting example, it will be appreciated by those skilled in the art that particular features or characteristics described in reference to one figure or embodiment may be combined as suitable with features or characteristics described in another figure or embodiment. Applicant regards the subject matter of the application to include all combinations and sub-combinations of the various steps, elements, features, functions, and/or properties disclosed herein.

What is claimed is:

1. A computer-implemented method for determining when to undergo a hair transplantation, the method comprising:

determining a hair loss value associated with a body surface based on identified regions, the regions comprising one or more potential donor areas and one or more potential recipient areas;

automatically analyzing, using computer image processing, proportions of classes of follicular units within the one or more potential donor areas and the one or more potential recipient areas, wherein automatically analyzing, using computer image processing, proportions of classes of follicular units comprises classifying follicular units based on the number of hairs or hair follicles in a follicular unit; and automatically, via a processor, determining when a hair transplantation procedure is recommended based, at least in part, on the determined hair loss value and the results of automatically analyzing proportions of classes.

2. The computer-implemented method of claim 1, further comprising automatically determining, using computer image processing, a proportion of terminal and/or non-terminal hair within the one or more potential donor areas and the one or more potential recipient area, and wherein automatically determining when a hair transplantation procedure is recommended is based, at least in part, on the determined portion of the terminal and/or non-terminal hair within the one or more potential donor areas and the one or more potential recipient area.

3. The computer-implemented method of claim 1, wherein hairs or hair follicles in a follicular unit that are determined to be non-terminal are not counted in the classification.

4. A system for determining when to undergo a hair transplantation, the system comprising:

at least one non-transitory storage medium storing instructions; and one or more processors for executing operations on image data, the one or more processors executing instructions for;

automatically analyzing, using computer image processing, proportions of classes of follicular units within the one or more potential donor areas and the one or more potential recipient areas, wherein automatically analyzing, using computer image processing, proportions of classes of follicular units comprises classifying follicular units based on the number of hairs or hair follicles in a follicular unit; and automatically, via the one or more processors, determining when a hair transplantation procedure is recommended based, at least in part, on the determined hair loss value and the results of automatically analyzing proportions of classes.

5. The system of claim 4, further comprising automatically determining, using computer image processing, a proportion of terminal and/or non-terminal hair within the one or more potential donor areas and the one or more potential recipient area, and wherein automatically determining when a hair transplantation procedure is recommended is based, at least in part, on the determined portion of the terminal and/or non-terminal hair within the one or more potential donor areas and the one or more potential recipient area.

6. The system of claim 4, wherein hairs or hair follicles in a follicular unit that are determined to be non-terminal are not counted in the classification.

* * * * *